United States Patent
Aikawa

(10) Patent No.: US 9,645,413 B2
(45) Date of Patent: May 9, 2017

(54) LINE OF SIGHT DETECTION DEVICE, DISPLAY METHOD, LINE OF SIGHT DETECTION DEVICE CALIBRATION METHOD, SPECTACLE LENS DESIGN METHOD, SPECTACLE LENS SELECTION METHOD, SPECTACLE LENS MANUFACTURING METHOD, PRINTED MATTER, SPECTACLE LENS SALES METHOD, OPTICAL DEVICE, LINE OF SIGHT INFORMATION DETECTION METHOD, OPTICAL INSTRUMENT DESIGN METHOD, OPTICAL INSTRUMENT, OPTICAL INSTRUMENT SELECTION METHOD, AND OPTICAL INSTRUMENT PRODUCTION METHOD

(71) Applicant: NIKON CORPORATION, Tokyo (JP)

(72) Inventor: Naoshi Aikawa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 100 days.

(21) Appl. No.: 14/661,457

(22) Filed: Mar. 18, 2015

(65) Prior Publication Data
US 2015/0286070 A1    Oct. 8, 2015

Related U.S. Application Data

(63) Continuation of application No. PCT/JP2013/075355, filed on Sep. 19, 2013.

(30) Foreign Application Priority Data

Sep. 19, 2012  (JP) .................................. 2012-205451
Sep. 19, 2012  (JP) .................................. 2012-205452
Sep. 19, 2012  (JP) .................................. 2012-206099

(51) Int. Cl.
G02C 7/02    (2006.01)
G02C 13/00   (2006.01)
(Continued)

(52) U.S. Cl.
CPC ............ *G02C 7/027* (2013.01); *A61B 3/0091* (2013.01); *A61B 3/113* (2013.01);
(Continued)

(58) Field of Classification Search
CPC .......... G02C 7/02; G02C 7/024; G02C 7/025; G02C 7/027; G02C 7/061; G02C 7/066;
(Continued)

(56) References Cited

U.S. PATENT DOCUMENTS

| 5,305,764 A | 4/1994 | Yamada et al. |
| 5,699,108 A | 12/1997 | Katayama et al. |

(Continued)

FOREIGN PATENT DOCUMENTS

| EP | 2 340 760 A1 | 7/2011 |
| JP | 4-049943 | 2/1992 |

(Continued)

OTHER PUBLICATIONS

Extended European Search Report issued by the European Patent Office in European Application No. 13839684.1, mailed Apr. 20, 2016.

(Continued)

*Primary Examiner* — Scott J Sugarman
*Assistant Examiner* — Ibrahima Diedhiou
(74) *Attorney, Agent, or Firm* — Finnegan, Henderson, Farabow, Garrett & Dunner, LLP

(57) ABSTRACT

A line of sight detection device calibration method, which calibrates a line of sight detection device that measures movement of an eyeball of a subject wearing eyeglasses and detects a transmission point at which a line of sight of the (Continued)

subject passes through a lens of the eyeglasses based on a result of measurement, includes: a measurement step of measuring the movement of the eyeball of the subject in a condition in which a first baseline is arranged at a predetermined position relative to the lens of the eyeglasses and the first baseline reflected in a corner cube substantially corresponds to a second baseline of the corner cube; and a calibration step of calibrating the line of sight detection device based on a result of measurement by the measurement step.

17 Claims, 37 Drawing Sheets

(51) Int. Cl.
  *G02B 27/00* (2006.01)
  *A61B 3/00* (2006.01)
  *A61B 3/113* (2006.01)
(52) U.S. Cl.
  CPC ......... *G02B 27/0093* (2013.01); *G02C 7/025* (2013.01); *G02C 13/005* (2013.01)
(58) Field of Classification Search
  CPC ... G02C 13/005; G02B 27/0093; G06F 3/013; G03B 13/02; G09B 23/28; A61B 3/0091; A61B 3/024; A61B 3/113; B24B 13/0055; H04N 13/0003
  USPC .... 51/41, 159.42, 159.74, 159.76, 204, 206, 51/209, 246; 348/208.15, 207.99; 396/51; 703/6
  See application file for complete search history.

(56) References Cited

U.S. PATENT DOCUMENTS

| | | | |
|---|---|---|---|
| 5,758,201 A | 5/1998 | Watanabe et al. | |
| 2004/0189935 A1 | 9/2004 | Warden et al. | |
| 2009/0248377 A1 | 10/2009 | Shinohara et al. | |
| 2010/0141893 A1 | 6/2010 | Altheimer et al. | |
| 2011/0007269 A1 | 1/2011 | Trumm et al. | |
| 2011/0157549 A1 | 6/2011 | Wada | |
| 2011/0222019 A1 | 9/2011 | Suzuki et al. | |
| 2011/0242486 A1 | 10/2011 | Ebisawa | |

FOREIGN PATENT DOCUMENTS

| | | | |
|---|---|---|---|
| JP | 5-100147 | 4/1993 | |
| JP | 6-53107 | 7/1994 | |
| JP | 8-563 | 1/1996 | |
| JP | 7-72600 | 3/1996 | |
| JP | 9-211376 | 8/1997 | |
| JP | 10-66678 | 3/1998 | |
| JP | 2000-5130 | 1/2000 | |
| JP | 2007-136000 | 6/2007 | |
| JP | 2008-521027 | 6/2008 | |
| JP | 2008-212718 | 9/2008 | |
| JP | 2009-259213 | 11/2009 | |
| JP | 2010-517087 | 5/2010 | |
| JP | 2010-259605 | 11/2010 | |
| JP | 2011-133064 | 7/2011 | |
| JP | 2011-206542 | 10/2011 | |
| JP | 2012-022288 | 2/2012 | |
| WO | WO 2006/054985 | 5/2006 | |
| WO | WO 2006/054985 A1 | 5/2006 | |
| WO | WO 2006054985 A1 * | 5/2006 | ............... G02C 7/02 |
| WO | WO 2009/086860 A1 | 7/2009 | |

OTHER PUBLICATIONS

International Search Report issued by the Japanese Patent Office in International Application No. PCT/JP2013/075355, mailed Dec. 17, 2013 (5 pages).

International Preliminary Report and Written Opinion issued by the Japanese Patent Office in International Application No. PCT/JP2013/075355, mailed Dec. 17, 2013 (21 pages).

Office Action issued by Japanese Patent Office in counterpart Japanese Patent Application No. JP-2014-536917 dated Jun. 21, 2016, and English Translation thereof.

* cited by examiner

LINE OF SIGHT DETECTION DEVICE, DISPLAY METHOD, LINE OF SIGHT DETECTION DEVICE CALIBRATION METHOD, SPECTACLE LENS DESIGN METHOD, SPECTACLE LENS SELECTION METHOD, SPECTACLE LENS MANUFACTURING METHOD, PRINTED MATTER, SPECTACLE LENS SALES METHOD, OPTICAL DEVICE, LINE OF SIGHT INFORMATION DETECTION METHOD, OPTICAL INSTRUMENT DESIGN METHOD, OPTICAL INSTRUMENT, OPTICAL INSTRUMENT SELECTION METHOD, AND OPTICAL INSTRUMENT PRODUCTION METHOD

This application is a continuation of International Application No. PCT/JP2013/075355 filed Sep. 19, 2013.

INCORPORATION BY REFERENCE

The disclosures of the following priority applications and the International Application are herein incorporated by reference:
Japanese Patent Application No. 2012-205451 filed Sep. 19, 2012;
Japanese Patent Application No. 2012-205452 filed Sep. 19, 2012;
Japanese Patent Application No. 2012-206099 filed Sep. 19, 2012; and
International Application No. PCT/JP2013/075355 filed Sep. 19, 2013.

BACKGROUND OF THE INVENTION

Field of the Invention

The present invention relates to a line of sight detection device, a display method, a line of sight detection device calibration method, a spectacle lens design method, a spectacle lens selection method, a spectacle lens manufacturing method, a printed matter, a spectacle lens sales method, an optical device, a line of sight information detection method, an optical instrument design method, an optical instrument, an optical instrument selection method, and an optical instrument production method.

Description of Related Art

A design method is known which includes detecting the position of a transmission point at which a line of sight passes or passes through a lens of eyeglasses from data relating to movement of an eyeball obtained by measurement of a line of sight detection device and using this detection result in designing a spectacle lens (cf., Japanese Translation of PCT International Application Publication 2008-521027).

This conventional technology, which includes calibration on the relationship between data of movement of an eyeball (or eyeball movement data) and a transmission point, measures the movement of the eyeball as the line of sight passes through a known transmission point. Specifically, it uses an occluder made of a sheet having characteristics that is transparent to infrared used for measuring the eyeball movement data but is opaque to visible light, which is attached to the spectacle lens. This occluder is formed of a pinhole. The subject gazes an object, which is a target of gaze, through the pinhole; and the movement of the eyeball of the subject in this condition is measured to give eyeball movement data. Thus, the eyeball movement data when the line of sight passes through the known transmission point (i.e., pinhole) is measured.

This conventional line of sight detection device includes an eyeball imaging camera and obtains line of sight information such as a gaze point and a direction of line of sight based on the image of pupil obtained by the camera. Also, to further increase the precision of the line of sight information, a conventional technique irradiates infrared light to the front side of the eyeball, captures an image of the infrared light source reflected at the cornea by the eyeball imaging camera, and calculates, for instance, gaze point and direction of line of sight using the image of pupil and the image of the infrared light source reflected at the cornea.

For instance, Japanese Examined Patent Publication H06-53107 discloses a conventional line of sight detection device of the type in which the eyeball imaging camera is put on the photographed person himself. Japanese Examined Patent Publication H06-53107 discloses the construction including a goggle having a portion attached to the head of the photographed person from which portion extends a fixed portion at which the eyeball imaging camera that captures an image of pupil is attached.

This construction involves a so-called calibration state in which an image of eyeball of the subject who gazes at two to nine marks placed in front of him is captured. After the calibration is finished, it is possible to calculate which direction the subject sees based on an image of eyeball of the subject who faces in any desired direction and the image of eyeball obtained by the calibration. This enables calculation of the direction of line of sight, gaze point, and angle of rotation.

Japanese Laid-Open Patent Publication H10-66678 discloses a conventional eyeball imaging camera of the type in which the camera is not put on the photographed person himself but is of the stationary type which is placed, for instance, on a desk. Japanese Laid-Open Patent Publication H10-66678 discloses that the eyeball imaging camera, which is installed on a desk, captures an image of the eyeball of the subject. Regarding the method of calibration and calculation of the direction of line of sight in any desired direction after the calibration disclosed in Japanese Laid-Open Patent Publication H10-66678 are the same as those disclosed in Japanese Translation of PCT International Application Publication 2008-521027.

Although the technology of Japanese Laid-Open Patent Publication H10-66678 avoids need of putting the device on the subject himself, the detection of the eyeball alone fails to distinguish seeing sideward by rotating only the eyeballs from seeing sideward by rotation of the eyeballs along with rotation of the head and thus fails to calculate accurate angle of rotation and line of sight direction vector. Consequently, a camera for head is separately used to observe markers attached to the head as means for detecting the movement of the head. As described above, most of such desktop type devices need means for head detection means for detecting the movement of the head.

Upon performing such a calibration, a calibration coefficient is calculated based on information about movement of the eyeball (hereafter, eyeball movement information) of a subject who gazes at a plurality of marks the subject gazes at a plurality of marks and on the position coordinates data of the marks on an image of the forward field of view camera used for capturing the image. Then, calibration is performed using the calculated calibration coefficient so that the eyeball movement information matches with the gaze position. The calibration coefficient includes elements, for instance, error of position at which the line of sight detection device is attached to the subject and individual difference of physical form and physiological variation of the eyeball of the subject. The physical form of the eyeball includes, for instance, size of the eyeball and asphericity of cornea surface. Japanese Laid-Open Patent Publication 2000-5130 discloses a method of calculating these calibration coefficients dividedly component by component. Thus, it is difficult to completely avoid influences of the sheet on the line of sight of the subject and on the result of measurement by the line of sight detection device; some error tends to occur. The pinhole of the sheet is small, which makes the range of view narrow and unclear.

SUMMARY OF THE INVENTION

In the above-described conventional technology, a diagram is prepared by plotting the detected positions two-dimensionally. However, this diagram is insufficient as a display method since no construction is adopted as to what display is useful for design and selection of spectacle lenses.

In the above-described conventional technologies, the sheet need be applied to a wide range on a spectacle lens. This makes it difficult to completely avoid influences of the sheet on the line of sight of the subject and on the result of measurement by the line of sight detection device and allows for some errors of measurement to occur. In addition, the pinhole is small and thus the range of view is narrow and unclear. The object to be gazed and the pinhole in the sheet applied to the spectacle lens have considerably different distances from the eye of the subject, so that the boundary of the pinhole is unclear. These allow prediction of low precision of measurement. Consequently, the conventional technology may have low precision of calibration.

The conventional line of sight detection device described above is not configured to cope with the condition that the subject wears an optical instrument, such as eyeglasses, that refracts light to enter the eyeball.

The conventional technologies calibrate eyeball movement information only in a region near the center of the field of view of a subject wearing eyeglasses with distribution of refractive power differing locally, such as progressive power eyeglasses, or eyeglasses with high refractive power. At the peripheral part or the progressive power region, calibration of the eyeball movement information is below completeness; sometimes it is difficult to accurately identify the point at which the line of sight passes on the progressive spectacle lens.

According to the 1st aspect of the present invention, a line of sight detection device, comprises: a measurement unit that measures a movement of eyeball of a subject wearing eyeglasses; a gaze point detection unit that detects a gaze point of the subject in a forward field of view of the subject based on a result of measurement by the measurement unit; a transmission point detection unit that detects a transmission point at which a line of sight of the subject toward the gaze point passes through a lens of the eyeglasses based on the result of the measurement by the measurement unit; and a display control unit that causes gaze point information indicating a position of the gaze point to be displayed at a display in superimposition on an image of the forward field of view and causes transmission point information indicating a position of the transmission point to be displayed at the display in superimposition on a lens image showing the lens of the eyeglasses.

According to the 2nd aspect of the present invention, in the line of sight detection device according to the 1st aspect, it is preferred that the display control unit causes the image of the forward field of view and the lens image to be displayed in superimposition one on another by causing the gaze point information and the transmission point information to be displayed in superimposition one on another.

According to the 3rd aspect of the present invention, in the line of sight detection device according to the 1st aspect, it is preferred that the display control unit causes the image of the forward field of view on which the gaze point information is superimposed and the lens image on which the transmission point information is superimposed to be displayed in separate regions from each other.

According to the 4th aspect of the present invention, in the line of sight detection device according to any one of the 1st to 3rd aspects, it is preferred that the transmission point detection unit detects a left side transmission point, at which the line of sight passes through a left side lens of the eyeglasses and a right side transmission point, at which the line of sight passes through a right side lens of the eyeglasses, the display control unit causes left side transmission point information indicating a position of the left side transmission point to be displayed at the display unit in superimposition on a left side lens image indicating a position of the left side lens and causes right side transmission point information indicating a position of the right side transmission point at the display unit in superimposition on a right side lens image showing the right side lens.

According to the 5th aspect of the present invention, in the line of sight detection device according to any one of the 1st to 4th aspects, it is preferred that the lens image is an image that shows a characteristic of the lens.

According to the 6th aspect of the present invention, in the line of sight detection device according to any one of the 1st to 5th aspects, it is preferred that the display control unit causes a graph relating to the gaze point or the transmission point to be displayed in juxtaposition with the image of the forward field of view on which the gaze point information is superimposed or the lens image on which the transmission point information is superimposed.

According to the 7th aspect of the present invention, in the line of sight detection device according to the 6th aspect, it is preferred that the graph indicates a distance from the eyeball of the subject to the gaze point.

According to the 8th aspect of the present invention, in the line of sight detection device according to the 6th aspect, it is preferred that the graph indicates the characteristic of the lens at the transmission point.

According to the 9th aspect of the present invention, a display method comprises: causing gaze point information indicating a position of a gaze point of a subject wearing eyeglasses to be displayed at a display unit in superimposition on an image of a forward field of view of the subject; and causing transmission point information indicating a position of a transmission point at which a line of sight of the subject toward the gaze point passes through a lens of the eyeglasses to be displayed at the display unit in superimposition on a lens image indicating the lens of the eyeglasses.

According to the 10th aspect of the present invention, a spectacle lens design method comprises: analyzing the gaze point information and the transmission point information obtained by the line of sight detection device according to any one of the 1st to 8th aspects; and designing a lens of eyeglasses based on a result of the analyzing.

According to the 11th aspect of the present invention, a spectacle lens selection method comprises: analyzing the gaze point information and the transmission point information obtained by the line of sight detection device according to any one of the 1st to 8th aspects; and selecting at least one lens of eyeglasses out of a plurality of lenses of eyeglasses based on result of the analyzing.

According to the 12th aspect of the present invention, a spectacle lens manufacturing method comprises: analyzing the gaze point information and the transmission point information obtained by the line of sight detection device according to any one of the 1st to 8th aspects; and manufacturing a lens of eyeglasses based on a result of the analyzing.

According to the 13th aspect of the present invention, a printed matter comprises: the gaze point information obtained by the line of sight detection device according to any one of the 1st to 8th aspects superimposed on an image of the forward field of view and the transmission point information determined by the line of sight detection device according to any one of the 1st to 8th aspects superimposed on the lens image.

According to the 14th aspect of the present invention, a spectacle lens sales method comprises: explaining a characteristic of the lens of the eyeglasses using the printed matter according to the 13th aspect.

According to the 15th aspect of the present invention, a display method comprises: causing transmission point information indicating a position of a transmission point, at which a line of sight of a subject wearing a lens of eyeglasses passes through the lens, to be displayed at a display unit in superimposition on a lens image showing the lens of eyeglasses.

According to the 16th aspect of the present invention, in the display method according to the 15th aspect, it is preferred that the transmission point information indicates a transmission region in which at least one transmission point is located when the subject gazes at a predetermined region of a forward field of view of the subject, and the transmission region is displayed in a number of at least one.

According to the 17th aspect of the present invention, in the display method according to the 15th or 16th aspect, it is preferred that the lens image is any one of an image showing a shape of a lens before rounding, an image showing a shape of a frame of the eyeglasses, an image showing distribution of aberration of the lens of the eyeglasses or an image showing distribution of addition of the lens of the eyeglasses.

According to the 18th aspect of the present invention, a printed matter comprises: a lens image showing a lens of eyeglass a subject wears; and transmission point information, which indicates a position of transmission point, at which a line of sight of the subject passes through the lens of eyeglasses, wherein the transmission point information being superimposed on the lens image.

According to the 19th aspect of the present invention, in the printed matter according to the 18th aspect, it is preferred that the transmission point information indicates a transmission region in which at least one transmission point is located when the subject gazes at a predetermined region of a forward field of view of the subject, and the transmission region is printed in a number of at least one.

According to the 20th aspect of the present invention, in the printed matter according to the 18th or 19th aspect, it is preferred that the lens image is any one of an image showing a shape of a frame of the eyeglasses, an image showing a distribution of aberration of a lens of the eyeglasses, or an image showing a distribution of addition of the lens of the eyeglasses.

According to the 21st aspect of the present invention, a line of sight detection device comprises: a measurement unit that measures movement of an eyeball of a subject wearing eyeglasses; a transmission point detection unit that detects a transmission point at which a line of sight of the subject passes through a lens of eyeglasses based on a result of measurement by the measurement unit; and a display control unit that causes transmission point information, which indicates a position of the transmission point, to be displayed in superimposition on a lens image that shows the lens of the eyeglasses.

According to the 22nd aspect of the present invention, in the line of sight detection device according to the 1st or 21st aspect, it is preferred that the display control unit causes transmission point information detected based on a first measurement result obtained by the measurement unit and transmission point information detected based on a second measurement result obtained by the measurement unit to be displayed at a display unit in superimposition on the lens image.

According to the 23rd aspect of the present invention, a line of sight detection device comprises: a measurement unit that measures movement of an eyeball of a subject wearing eyeglasses; a gaze point detection unit that detects a gaze point of the subject in a forward field of view of the subject based on a result of measurement by the measurement unit; a transmission point detection unit that detects a transmission point at which a line of sight of the subject toward the gaze point passes through a lens of the eyeglasses based on the result of the measurement by the measurement unit; and a display control unit that causes gaze point information indicating a position of the gaze point to be displayed at a display in superimposition on an image of the forward field of view and causes transmission point information indicating a position of the transmission point to be displayed at the display unit.

According to the 24th aspect of the present invention, a display method comprises: causing gaze point information indicating a position of a gaze point of a subject wearing eyeglasses to be displayed at a display unit in superimposition on an image of a forward field of view of the subject; and causing transmission point information indicating a position of a transmission point at which a line of sight of the subject toward the gaze point passes through the lens of the eyeglasses to be displayed at the display unit.

According to the 25th aspect of the present invention, an optical device comprises: a calibration computation unit that calculates line of sight information based on movement information of an eyeball of a subject and corrects an error of the line of sight information due to a refractive action at an optical instrument the subject wears.

According to the 26th aspect of the present invention, in the optical device according to the 25th aspect, it is preferred that the calibration computation unit includes a first calibration computation unit that calculates the line of sight information of a subject based on the movement information of the eyeball of the subject and a second calibration computation unit that that corrects an error of the line of sight information due to a refractive action at an optical instrument the subject wears.

According to the 27th aspect of the present invention, in the optical device according to the 25th or 26th aspect, it is preferred that the line of sight information is a gaze point of the subject.

According to the 28th aspect of the present invention, in the optical device according to any one of the 25th to 27th aspects, it is preferred that the line of sight information is a transmission point of the line of sight of the subject at the optical instrument.

According to the 29th aspect of the present invention, in the optical device according to any one of the 25th to 28th aspects, it is preferred that the optical instrument is a spectacle lens.

According to the 30th aspect of the present invention, in the optical device according to the 29th aspect, it is preferred that the spectacle lens has a different refractive power at a different region of the spectacle lens.

According to the 31st aspect of the present invention, in the optical device according to the 29th or 30th aspect, it is preferred that the spectacle lens is a progressive power spectacle lens.

According to the 32nd aspect of the present invention, in the optical device according to any one of the 25th to 31st aspects, it is preferred that the calibration computation unit computes using a conversion formula containing a term of a third order or higher and corrects an error of the line of sight information based on the movement information of the eyeball.

According to the 33rd aspect of the present invention, in the optical device according to any one of the 25th to 32nd aspects, it is preferred that the calibration computation unit calculates, substantially at the same time, a piece of the line of sight information that is the gaze point of the subject and a piece of the line of sight information that is the transmission point of the line of sight of the subject at the optical instrument corresponding to the gaze point.

According to the 34th aspect of the present invention, in the optical device according to the 33rd aspect, it is preferred that the calibration computation unit calculates the gaze point and the transmission point corresponding to the gaze point substantially simultaneously with the measurement of the movement information of the eyeball.

According to the 35th aspect of the present invention, in the optical device according to any one of the 25th to 34th aspects, it is preferred that the calibration computation unit corrects an error of the line of sight information based on the movement information of the eyeball at a measurement point, which is arranged in a non-uniform density in the field of view of the subject.

According to the 36th aspect of the present invention, in the optical device according to any one of the 25th to 35th aspects, it is preferred that the calibration computation unit calculates an error of the line of sight information of the subject based on the movement information of the eyeball at a measurement point, which is arranged in a variable number in the field of view of the subject.

According to the 37th aspect of the present invention, in the optical device according to the 25th aspect, it is preferred that the calibration computation unit obtains in advance calibrated conversion formulas relating to the gaze point of the subject and the transmission point corresponding to the gaze point of the subject, and outputs data relating to the gaze point and the transmission point based on the movement information of the eyeball of the subject using the calibrated conversion formulas.

According to the 38th aspect of the present invention, in the optical device according to any one of the 25th to 37th aspects, it is preferred that the calibration computation unit performs measurement for calibration within a range of which a maximum angle of view exceeds 60 degrees.

According to the 39th aspect of the present invention, a line of sight information detection method comprises: a first calibration computation step of calculating line of sight information of a subject based on movement information of an eyeball of the subject; and a second calibration computation step of correcting an error of the line of sight information due to an optical instrument the subject wears.

According to the 40th aspect of the present invention, in the line of sight information method according to the 37th aspect, it is preferred that the line of sight information is a transmission point, at which a line of sight of the subject wearing eyeglasses passes through a lens of the eyeglasses, and the movement information of the eyeball of the subject is acquired in a condition such that a first baseline is arranged at a predetermined position relative to the lens of the eyeglasses and the first baseline reflected in a corner cube and a second baseline of the corner cube substantially correspond to each other.

According to the 41st aspect of the present invention, an optical instrument design method comprises: a first calibration computation step of calculating line of sight information of a subject based on movement information of an eyeball of the subject; a second calibration computation step of correcting an error of the line of sight information due to an optical instrument the subject wears; and a design step of designing the optical instrument based on the line of sight information.

According to the 42nd aspect of the present invention, an optical instrument designed by the design method according to the 41st aspect.

According to the 43rd aspect of the present invention, an optical instrument selection method comprises: a first calibration computation step of calculating line of sight information of a subject based on movement information of an eyeball of the subject; a second calibration computation step of correcting an error of the line of sight information due to an optical instrument the subject wears; and a selection step of selecting an optical instrument the subject wears from a plurality of optical instruments based on the line of sight information.

According to the 44th aspect of the present invention, an optical instrument production method comprises: a first calibration computation step of calculating line of sight information of a subject based on movement information of an eyeball of the subject; a second calibration computation step of correcting an error of the line of sight information due to an optical instrument the subject wears; a design step of designing the optical instrument based on the line of sight information; and a processing step of processing the optical instrument based on design in the design step.

According to the 45th aspect of the present invention, a line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, comprises: a measurement step of measuring the movement of the eyeball of the subject in a condition in which a first baseline is arranged at a predetermined position relative to the lens of the eyeglasses and the first baseline reflected in a corner cube substantially corresponds to a second baseline of the corner cube; and a calibration step of calibrating the line of sight detection device based on a result of measurement by the measurement step.

According to the 46th aspect of the present invention, in the line of sight detection device calibration method according to the 45th aspect, it is preferred that the first and the second baselines are baselines in at least two different directions, respectively.

According to the 47th aspect of the present invention, in the line of sight detection device calibration method according to the 45th or 46th aspect, it is preferred that in the measurement step, the movement of the eyeball of the subject is measured in a condition in which the subject gazes at the corner cube and the first baseline reflected in the corner cube substantially corresponds to the second baseline of the corner cube.

According to the 48th aspect of the present invention, in the line of sight detection device calibration method according to any one of the 45th to 47th aspects, it is preferred that the second baseline is a ridgeline of the corner cube.

According to the 49th aspect of the present invention, in the line of sight detection device calibration method according to any one of the 45th to 48th aspects, it is preferred that the first baseline is arranged at an outer peripheral part of the lens of eyeglass.

According to the 50th aspect of the present invention, in the line of sight detection device calibration method according to the 49th aspect, it is preferred that the first baseline is depicted on a reference member attached to the outer peripheral part of the lens of the eyeglasses.

According to the 51st aspect of the present invention, in the line of sight detection device calibration method according to the 49th aspect, it is preferred that the eyeglasses are a frame for ocular examination and the first baseline is depicted on the frame for ocular examination.

According to the 52nd aspect of the present invention, a line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, comprises: a detection step of detecting a position of a corner cube in a condition in which a first baseline is arranged at a predetermined position relative to the lens of the eyeglasses and the first baseline reflected in the corner cube substantially corresponds to a second baseline of the corner cube; and a calibration step of calibrating the line of sight detection device with respect to the transmission point based on a result of detection by the detection step.

According to the 53rd aspect of the present invention, a line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, comprises: a detection step of detecting a gaze point of the subject in a condition in which a first baseline is arranged at a predetermined position relative to the lens of the eyeglasses, the subject gazes at a corner cube, and the first baseline reflected in the corner cube substantially corresponds to a second baseline of the corner cube; and a calibration step of calibrating the line of sight detection device with respect to the transmission point based on the result of the detection by the detection step.

According to the 54th aspect of the present invention, a line of sight detection device measures movement of an eyeball of a subject wearing eyeglasses and detects a transmission point at which a line of sight of the subject passes through a lens of the eyeglasses based on a result of measurement, wherein the device is calibrated by the line of sight detection method according to any one of the 45th to 53rd aspects.

According to the 55th aspect of the present invention, a spectacle lens design method comprises: analyzing data of the transmission point obtained by the line of sight detection device according to the 54th aspect; and designing a lens of eyeglasses based on a result of the analyzing.

According to the 56th aspect of the present invention, a spectacle lens selection method comprises: analyzing data of the transmission point obtained by the line of sight detection device according to the 54th aspect; and selecting at least one lens of eyeglasses among a plurality of lenses of eyeglasses based on a result of the analyzing.

According to the 57th aspect of the present invention, a spectacle lens manufacturing method comprises: analyzing data of the transmission point obtained by the line of sight detection device according to the 54th aspect; and manufacturing a lens of eyeglasses based on a result of the analyzing.

According to the 58th aspect of the present invention, in the optical device according to the 25th or 26th aspect, it is preferred that the calibration computation unit performs measurement for calibration based on the movement information of the eyeball at nine and more measurement points within a range of which a maximum angle of view exceeds 60 degrees.

According to one embodiment of the present invention, display of the position of the detected point of transmission on the spectacle lens can be achieved in a useful form upon design or selection of spectacle lenses.

According to another embodiment of the present invention, calibration of the point of transmission can be achieved with high precision.

According to another embodiment of the present invention, a contribution can be made to detection of more accurate line of sight information.

DESCRIPTION OF EMBODIMENTS

First Embodiment

Figure 1:
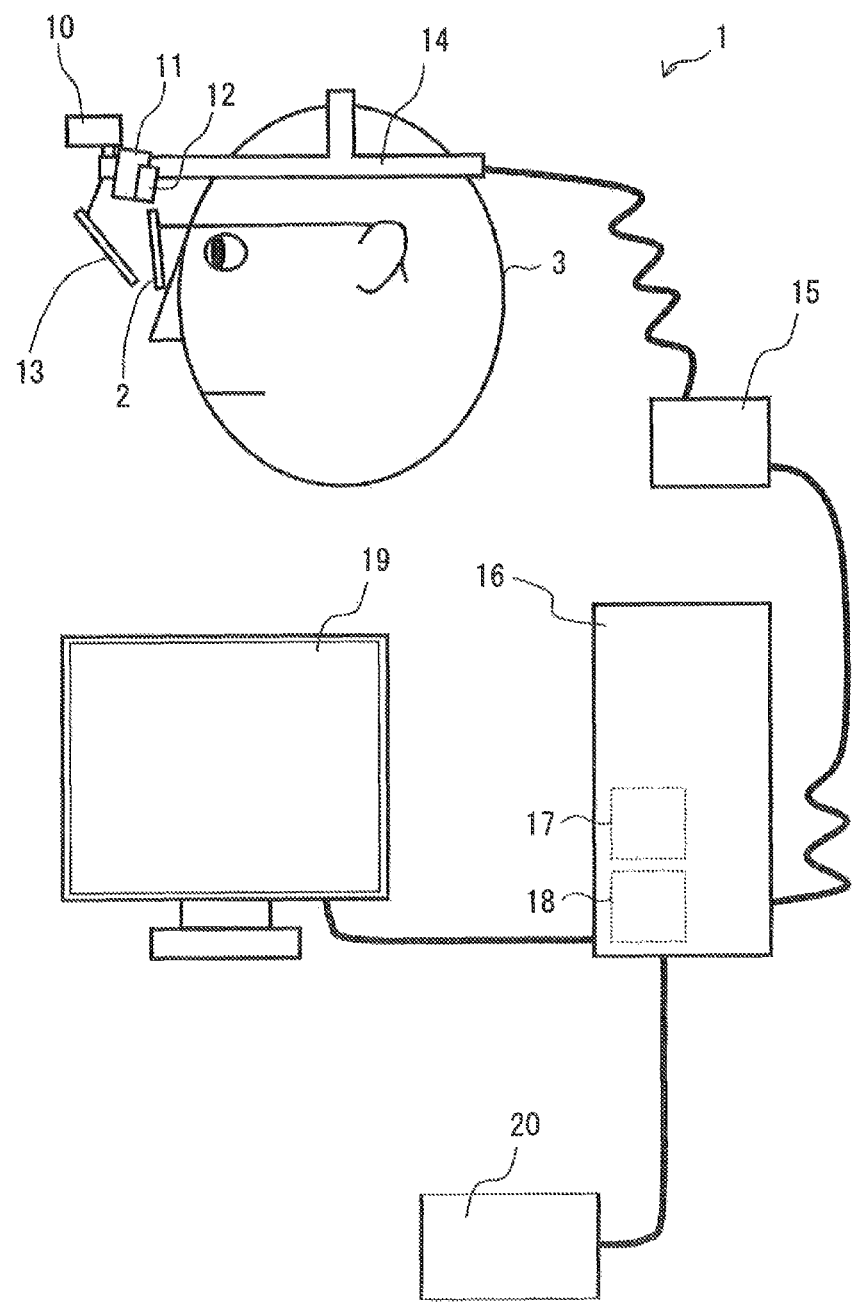
FIG. 1 is a diagram illustrating the construction of a line of sight detection device according to a first embodiment of the present invention.

Referring to the attached drawings, a first embodiment of the present invention is explained. FIG. 1 is a diagram illustrating the construction of a line of sight detection device 1 according to a first embodiment of the present invention. In FIG. 1, the line of sight detection device 1 detects the line of sight of the subject 3 wearing the eyeglasses 2.

The line of sight detection device 1 includes a forward field of view camera 10, an eyeball imaging camera 11, an infrared LED 12, a dichroic mirror 13, a headband 14, an image recording device 15, a personal computer (PC) 16, an image processing device 17, a calibration computation device 18, a monitor 19, a printer 20 and an unshown input device for the PC. In FIG. 1, the image recording device 15 is connected to the PC 16. However, the subject 3 may disconnect the image recording device 15 from the PC 16 and carry it with him.

The forward field of view camera 10, the eyeball imaging camera 11, the infrared light emitting diode (LED) 12, and the dichroic mirror 13 are attached to the headband 14. If the headband 14 is put on the head of the subject 3 wearing the eyeglasses 2, the dichroic mirror 13 is placed in front of the eyeglasses 2 and the forward field of view camera 10, the eyeball imaging camera 11, and the infrared LED 12 are placed above the eyeglasses 2.

The dichroic mirror 13 reflects infrared light and transmits visible light. Consequently, the subject 3 can freely see forward range of vision through the eyeglasses 2 and dichroic mirror 13 if he wears the headband 14.

In the condition in which the subject 3 wears the headband 14, the forward field of view camera 10 is fixed to face in a direction substantially the same as or slightly lower than the direction of the forward field of view of the subject 3 and can capture a moving image in the field of view in front of the subject 3 at a horizontal angle of view of about 90 degrees. The moving image captured by the forward field of view camera 10 is recorded at the image recording device 15.

The infrared light irradiated by the infrared LED 12 is reflected by the dichroic mirror 13 to illuminate the eyeball of the subject 3. The eyeball imaging camera 11 captures a moving image of the eyeball illuminated with the infrared light through the dichroic mirror 13 in the condition in which the pupil of the eyeball is brought into focus. The moving image captured by the eyeball imaging camera 11 is recorded at the image recording device 15. The eyeball imaging camera 11 is provided for each of the left and right eyes and these cameras capture separate moving images for left and right eyes, respectively. The moving image of the left eye and the moving image of the right eye are separately recorded at the image recording device 15.

The image of the forward field of view and the image of the eyeball, which are once recorded at the image recording device 15, are reproduced and output to the image processing device 17. The image processing device 17 performs arithmetic processing on the image of eyeball inputted from the image recording device 15 and outputs the coordinates of center of pupil and the coordinates of center of cornea reflection in the image of eyeball as eyeball movement data in chronological order for each of the left and right eyes.

The calibration computation device 18 performs arithmetic processing on the eyeball movement data outputted from the image processing device 17 and outputs the coordinates of the gaze point in the image of the forward field of view as gaze position data and the coordinates of a point at which the line of sight of the subject 3 toward the gaze point passes through the eyeglasses 2 (hereafter, referred to as "transmission point") as transmission position data. The gaze point and the transmission point are calculated for each of the left and right eyes. Usually, the gaze point is at the same position for both the left and right eyes. The coordinates of the transmission point are coordinates of the eyeglasses 2 at the lens surface. The surface at which the transmission point is measured may be either the front surface or the rear surface of the eyeglasses 2. For any aspheric lens, in particular any progressive power lens, a reference surface in the design of such lens may be used. This is more advantageous for design than other surfaces.

The PC 16 is configured to incorporate all of data, for instance, the image of forward field of view, the image of eyeball and the eyeball movement data outputted from the image processing device 17 and the gaze position data and the transmission position data outputted from the calibration computation device 18.

The PC 16 is configured to display the incorporated data, for instance, the eyeball movement data, the gaze position data, and the transmission position data on the monitor 19, record such data at the unshown recording medium, such as hard disk drive (HD), and output such data to the printer 20.

The PC 16 is further configured to display, for instance, an image obtained by overlaying a mark indicating the position of the gaze point on the image of forward field of view, or a cumulative frequency map of the gaze point on the monitor 19, to record such at the unshown recording medium such as HD, or to output such to the printer 20.

The PC 16 is further configured to display, for instance, an image obtained by overlaying a mark indicating the position of transmission point on the image of lens (or lens image) of the eyeglasses 2, or a cumulative frequency map of the transmission point on the monitor 19, to record such at the unshown recording medium such as HD, or to output such to the printer 20.

The printer 20 prints various types of data or images inputted from the PC 16 on paper.

In the above explanation, the image of eyeball captured by the eyeball imaging camera 11 is once recorded at the image recording device 15 and then reproduced and sent to the image processing device 17. However, the captured image may be recorded at the image recording device 15 and at the same time sent to the image processing device 17. This enables one to obtain gaze position data and transition position data simultaneously with the measurement of the line of sight.

The calibration computation device 18 described above obtains gaze position data from the eyeball movement data measured by the image processing device 17 using the relationship between the eyeball movement data and the gaze position data calibrated in advance. Further, the device 18 obtains transmission position data from the eyeball movement data measured by the image processing device 17 using the relationship between the eyeball movement data and the transmission position date calibrated in advance. The relationship between the eyeball movement data and the gaze position data and the relationship between the eyeball movement data and the transmission position data are calibrated in advance for each of the left and right eyes. The method of calibration may be any method available for this purpose.

The line of sight detection device 1 according to this embodiment is featured in the method of displaying the gaze position data and transmission position data on the monitor 19 as explained in detail below.

First Display Method

Figure 2:
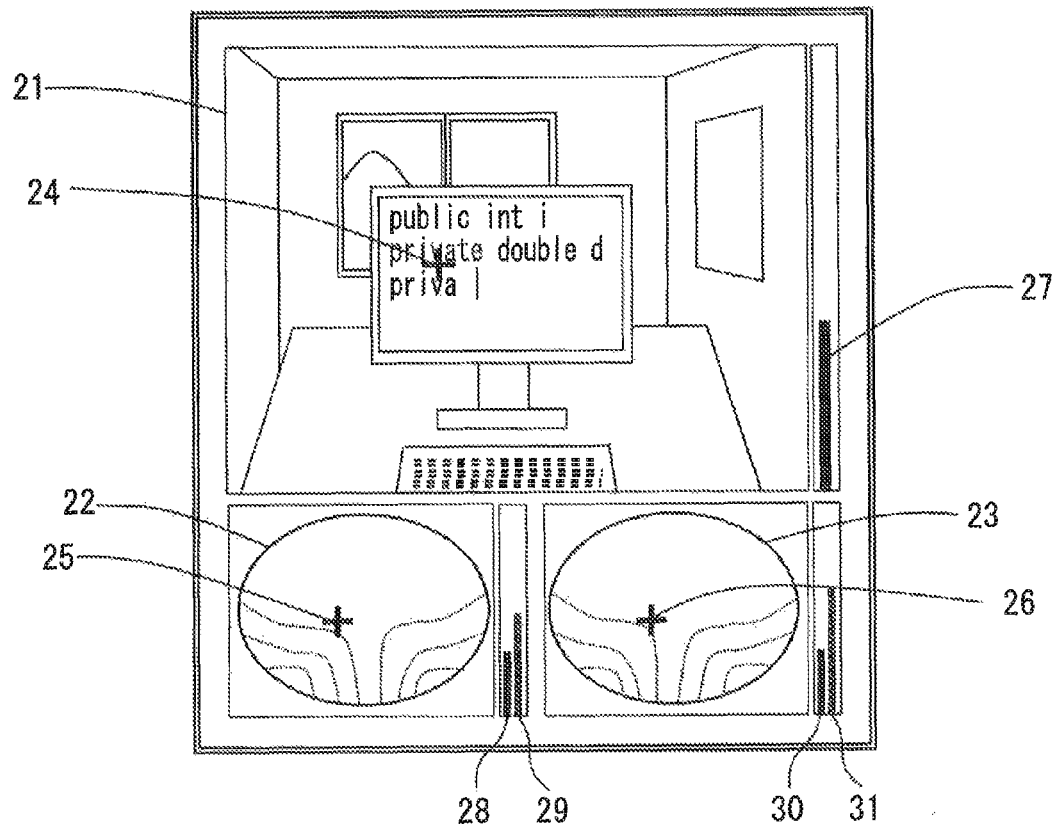
FIG. 2 is a diagram illustrating an example of a first display method in the first embodiment.

FIG. 2 is a diagram illustrating an example of a first display method in the first embodiment. The PC 16 causes the moving image 21 of the forward field of view captured by the forward field of view camera 10, a left lens image 22 showing the left side lens of the eyeglasses 2, and a right lens image 23 showing the right side lens of the eyeglasses 2 to be displayed in separate regions simultaneously in the frame displayed on the monitor 19. The left lens image 22 and the right lens image 23 represent each an image of a curve showing the shape of a lens frame inside of which level lines or contour lines showing the distribution of astigmatism are depicted. The lenses of the eyeglasses 2 in this embodiment are, for instance, progressive power lenses. Consequently, the left lens image 22 and the right lens image 23 shown in FIG. 2 indicate that they have each a region with high astigmatism on the lower lateral part of the respective lenses.

The PC 16 causes gaze point marks 24 that show the positions of the gaze points to be displayed in superimposition on the moving image 21 of the forward field of view. Further, the PC 16 causes a left transmission point mark 25 that indicates the position of the transmission point of the left side lens of the eyeglasses 2 to be displayed in superimposition on the left lens image 22 and a right transmission point mark 26 that indicates the position of the transmission point of the right side lens of the eyeglasses 2 to be displayed in superimposition on the right side lens image 23.

The PC 16 causes a bar graph 27 representing a distance of the gaze point from the eyeball of the subject 3 to be displayed on the right-hand neighbor of the moving image 21 of the forward field of view. The distance of the gaze point from the eyeball of the subject 3 may be determined based on the angle of line of sight of the subject 3 detected on the basis of the eyeball movement data of the subject 3. The PC 16 causes both a bar graph 28 that represents addition (or add) at the transmission point of the left side lens of the eyeglasses 2 and a bar graph 29 that represents the amount of astigmatism at the transmission point to be displayed on the right-hand neighbor of the left lens image 22. Further, the PC 16 causes a bar graph 30 that represents addition at the transmission point of the right side lens of the eyeglasses 2 and a bar graph 31 that represents amount of astigmatism at the transmission point of the eyeglasses 2 on the right-hand neighbor of the right lens image 23.

The first display method enables clearly displaying the correspondence between the gaze point and the transmission point and the relationship between the distance of the eyeball of the subject 3 from the gaze point and the addition or the amount of astigmatism at the transmission point of the lens of the eyeglasses 2.

Second Display Method

Figure 3:
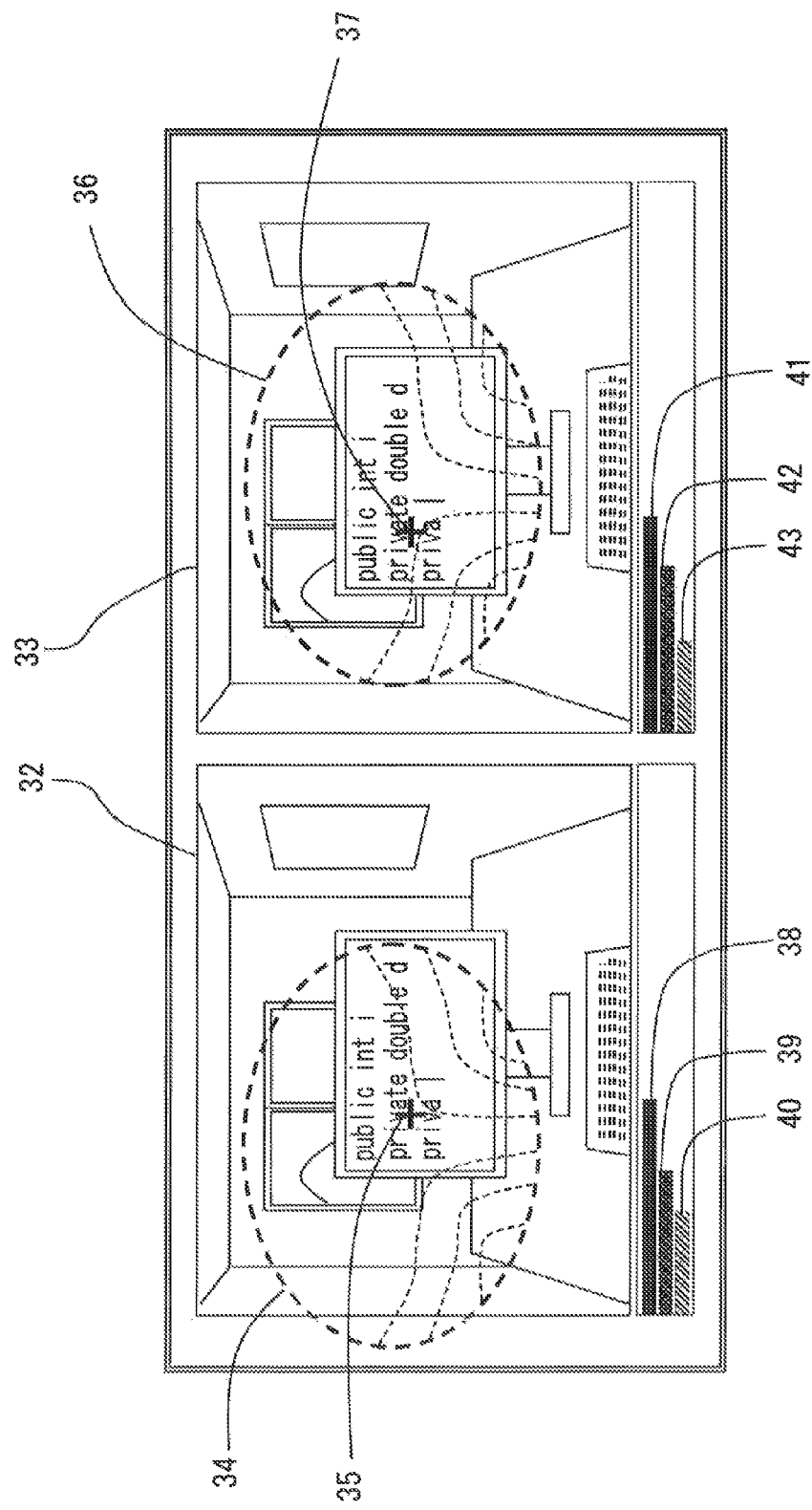
FIG. 3 is a diagram illustrating an example of a second display method in the first embodiment.
Figure 4:
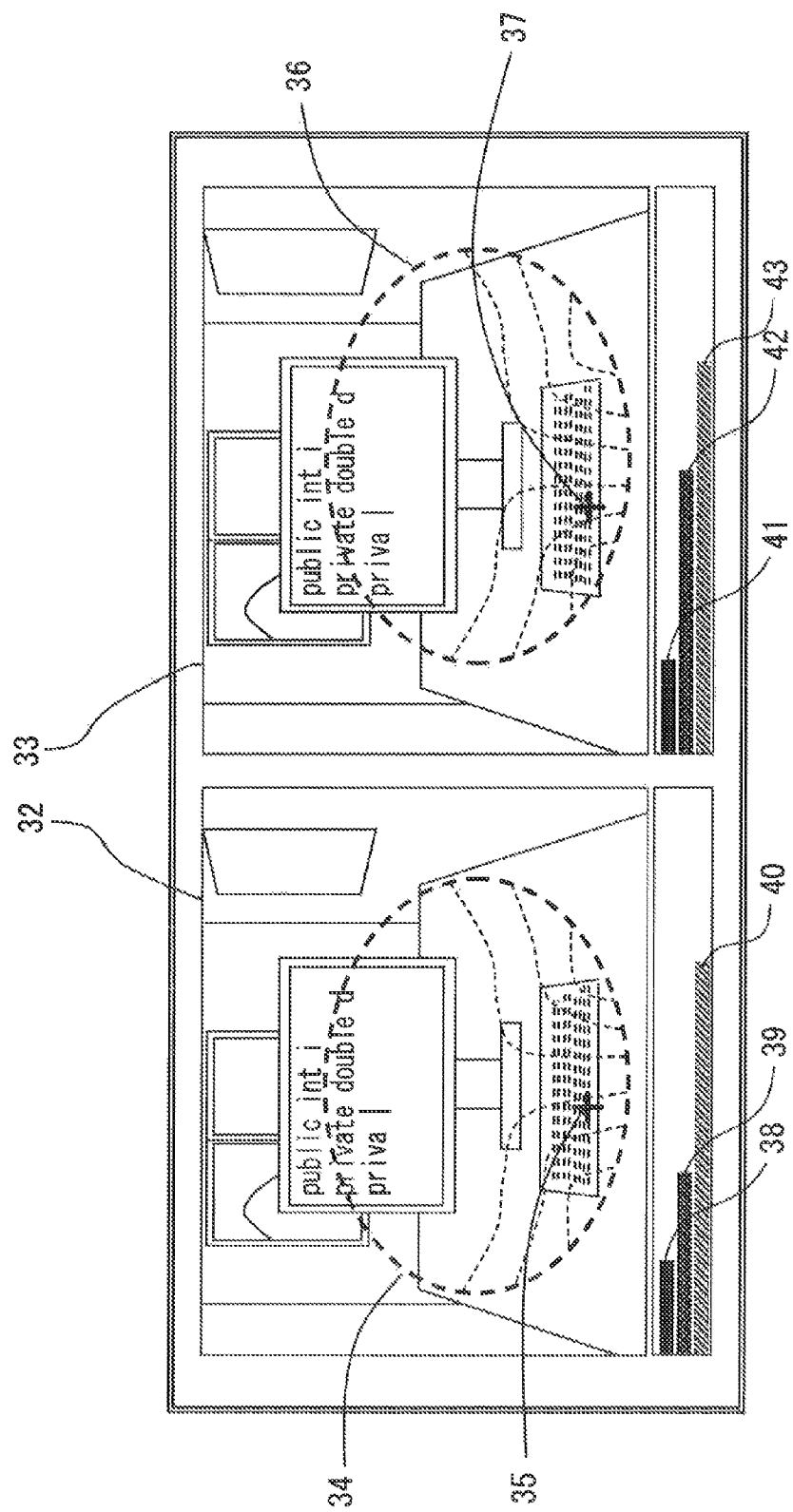
FIG. 4 is a diagram illustrating an example of a second display method in the first embodiment.

FIGS. 3 and 4 are diagrams illustrate each an example of a second display method used by the line of sight detection device 1. The PC 16 causes a moving image 32 of the forward field of view to be displayed on the left side within a frame displayed at the monitor 19 and a moving image 33 of the forward field of view to be displayed on the right side of the moving image 32 within the frame. The moving images 32 and 33 of the forward field of view are identical with each other.

The PC 16 causes a left lens image 34 to be displayed in superimposition on the moving image 32 of the forward field of view. The PC 16 causes the gaze point on the moving image 32 of the forward field of view and the transmission point on the left lens image 34 to be superimposed to the same position and a mark 35 that indicates the position of these points to be displayed. Similarly, the PC 16 causes a right lens image 36 to be displayed in superimposition on the moving image 33 of the forward field of view. On this occasion, the PC 16 causes the gaze point on the moving image 33 of the forward field of view and the transmission point on the right lens image 36 to be superimposed one on another to the same position and causes a mark 37 that indicates the position of these points to be displayed.

The PC 16 causes a bar graph 38 that represents a distance of the gaze point from the eyeball of the subject 3, a bar graph 39 that represents addition at the transmission point of the left side lens of the eyeglasses 2, and a bar graph 40 that represents the amount of astigmatism at that transmission point to be displayed side by side (in juxtaposition) on the downside of the moving image 32 of the forward field of view displayed on the left side.

Similarly, the PC 16 causes a bar graph 41 that represents a distance of the gaze point from the eyeball of the subject 3, a bar graph 42 that represents addition at the transmission point of the right side lens of the eyeglasses 2, and a bar graph 43 that represents the amount of astigmatism at that transmission point to be displayed side by side on the downside of the moving image 33 of the forward field of view displayed on the right side.

FIG. 3 illustrates an example of display in which the subject 3 gazes at a monitor of the PC placed on a desk (which is a monitor other than the line of sight detection device 1). FIG. 4 illustrates an example of display in which the subject 3, who moves the head and the line of sight downward, intending to gaze at the keyboard. The example of display shown in FIG. 3 confirms that the mark 35 indicating the gaze point and the mark 37 indicating the transmission point are disposed on the monitor of the PC and near the midpoint between the left lens image 34 and the right lens image 36. On the other hand, the example of display shown in FIG. 4 confirms that the mark 35 indicating the gaze point and the mark 37 indicating the transmission point are disposed on the keyboard and near the downsides of the left lens image 34 and the right lens image 36. The bar graphs 38 and 40 that represent each the distance of the gaze point from the eyeball of the subject 3, the bar graphs 39 and 42 that represent each an addition of the lens, and the bar graphs 40 and 43 that represent each the amount of astigmatism confirm that under the condition shown in FIG. 4 as compared with the condition shown in FIG. 3, the distance of the gaze point from the eyeball of the subject 3 is shorter and the addition is higher and the amount of astigmatism of the lens is larger.

As described above, the second display method clearly indicates the position of the transmission points on the lens of the eyeglasses 2 when the subject 3 gazes at the monitor and when he gazes at the keyboard and also differences in the amount of astigmatism at the transmission points. The second display method aids easier recognition of the relationship between the range of vision through the lens of the eyeglasses 2 of the subject 3 and the transmission point of the lens of the eyeglasses 2.

Now, the shape and size of the left lens image 34 and the right lens image 36 to be displayed in superimposition on the moving images 32 and 33 of the forward field of view are explained. Preferably, the size of the moving images 32 and 33 of the forward field of view and the size of the left lens image 34 and the right lens image 36 to be displayed in superimposition on the moving images 32 and 33, respectively, are relatively coordinated with the size of the lens frame in the field of view of the subject 3. This facilitates determination of approximate positional relationship between the transmission point on the spectacle lens (the eyeglass lens) and the forward field of view not only for gaze point viewed by central vision using the central retinal fovea, i.e., central area of the retina, but also for a region of peripheral vision near the gaze point.

However, due to a parallax between the field of view of the forward field of view camera 10 and that of the subject 3, the shape and size of the left lens image 34 and the right lens image 36 relative to the moving image 32 and 33 of the forward field of view vary, strictly in a complicated manner, depending on the size of and the distance from the subject 3 of an object imaged by the forward field of view camera 10. Thus it is difficult to display them in superimposition exactly. For simplification, the method includes determining display magnifications of the left lens 34 and the right lens image 36 with respect to the moving images 32 and 33, respectively, of the forward field of view near the gaze point, which serves as a reference, preparing a figure by simply proportionately magnifying the shape of the actual lens frame as a line representing the shape of the lens frame for the left lens image 34 and the right lens image 36, and causing the prepared line to be displayed in superimposition on the moving images 32 and 33, respectively, of the forward field of view.

In contrast, the left and right lens images may be displayed without adjustment of their size. For instance, display of the left lens image 34 and the right lens image 36 as expanded by setting their display magnification on the large side enables setting smaller contour interval that indicates the distribution of astigmatism in the lens to facilitate high precision display. This enables more accurate display of positional relationship between the distribution of astigmatism and the transmission point. Conversely, displaying the left lens image 34 and the right lens image 36 in a reduced size enables the left lens image 34 and the right lens image 36 in whole to be displayed within the frame at a narrower angle of view. However, it is preferred to use a uniform size for the left lens image 34 and the right lens image 36.

Third Display Method

Figure 5:
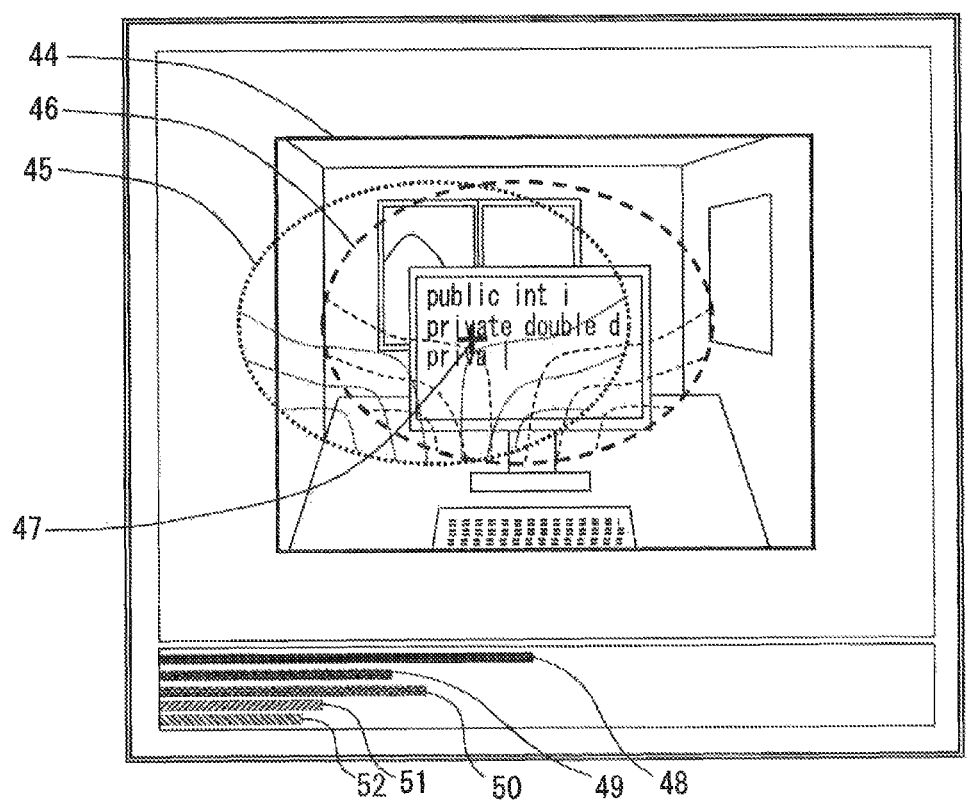
FIG. 5 is a diagram illustrating an example of a third display method in the first embodiment.

FIG. 5 is a diagram illustrating an example of a third display method using the line of sight detection device 1. The PC 16 causes a single moving image 44 of the forward field of view to be displayed within the frame displayed on the monitor 19. The PC 16 also causes a left lens image 45 and a right lens image 46 to be displayed in superimposition on the moving image 44 of the forward field of view. The left lens image 45 and the right lens image 46 have the same shape and size as those used in the second display method. The PC 16 causes the gaze point on the moving image 44 of the forward field of view, the transmission point on the left lens image 45, and the transmission point on the right lens image 46 to have the same position and a mark 47 indicating the position of these points to be displayed in superimposition.

The PC 16 causes five bar graphs, i.e., a bar graph 48 that represents the distance of the gaze point from the eyeball of the subject 3, a bar graph 49 that represents addition at the transmission point of the left side lens of the eyeglasses 2, a bar graph 50 that represents addition at the transmission point of the right side lens of the eyeglasses 2, a bar graph 51 that represents the amount of astigmatism at the transmission point of the left side lens, and a bar graph 52 that represents the amount of astigmatism at the transmission point of the right side lens to be displayed side by side on the downside of the moving image 44 of the forward field of view. Any region where the left lens image 45 and the right lens image 46 protrude from the moving image 44 of the forward field of view may be displayed as it is.

Figure 6:
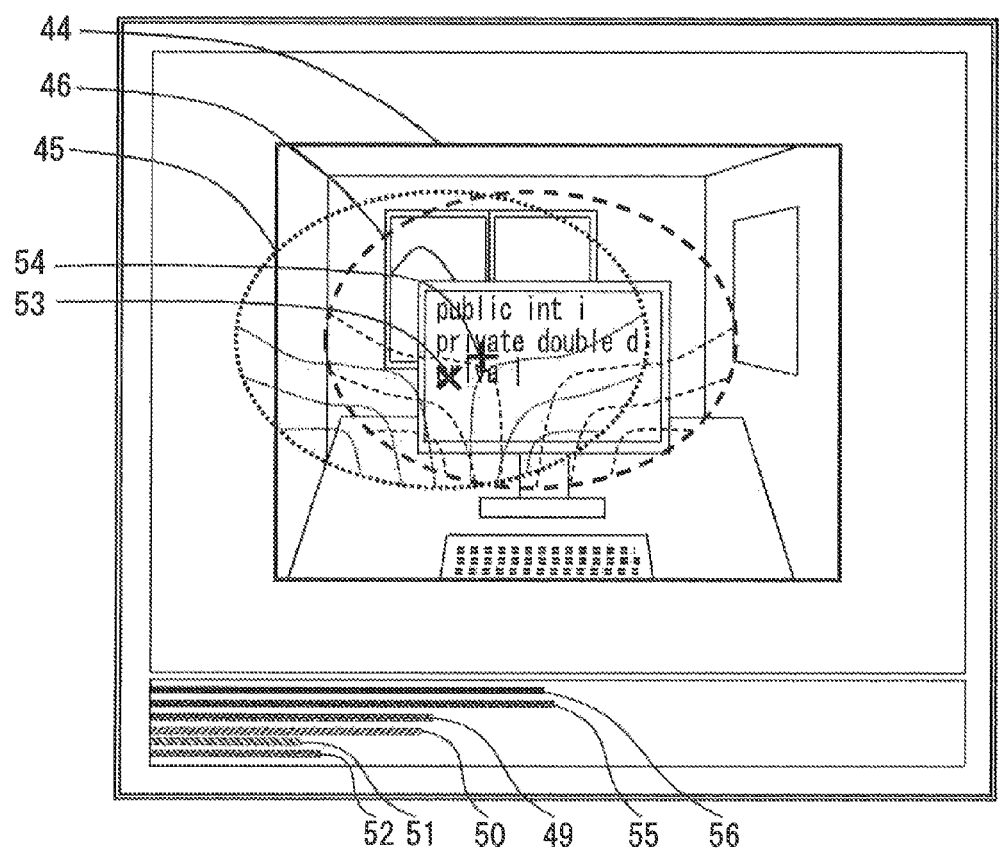
FIG. 6 is a diagram illustrating an example of a third display method in the first embodiment.

In the third display method, the gaze points 53 and 54 of the left and right eyes may be displayed independently from each other as shown in FIG. 6. In this case, in total six bar graphs, i.e., a bar graph 55 that represents the distance of the gaze point of the left eye from the eyeball of the left eye of the subject 3 and a bar graph 56 that represents the distance of the gaze point of the right eye from the eyeball of the right eye of the subject 3, and the bar graphs 49 to 52 mentioned above are displayed side by side. If the calibration has an error or if the subject has a disease such as strabismus or crossed eyes, the positions of the gaze points 53 and 54 may be different from each other. Thus, such an independent display helps one find such a phenomenon or disease.

The first to third display methods enables the correspondence between the position of the gaze point and the position of the transmission point to be displayed comprehensibly. This allows simple observation such as search for the tendency as to how the subject 3 uses the eyeglasses 2 or as to whether the lens of the eyeglasses 2 is used as the designer expected and thus enables the subject 3 to make best selection or design of the type of lens of the eyeglasses efficiently.

Design of Progressive Power Spectacle Lens

Figure 7:
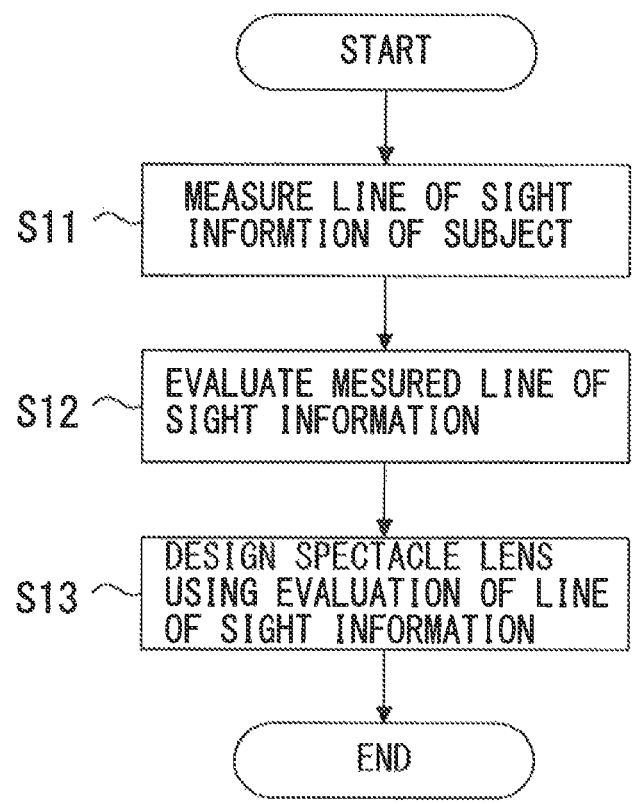
FIG. 7 is a flowchart illustrating a procedure of designing spectacle lenses.

Procedure of designing a novel progressive power spectacle lens using the result of measurement by the line of sight detection device 1 is explained referring to the flowchart illustrated in FIG. 7.

In step S11, the subject wearing a reference spectacle lens is put in a specified environment and the line of sight information (gaze position data and transmission position data) of the subject is measured by the line of sight detection device 1. The term "reference spectacle lens" is a spectacle lens which is used as a reference for designing a new progressive power spectacle lens. It may be, for instance, a trial model. The "specified environment" is one of environments in which a new progressive power spectacle lens will be used. It may be, for instance, an environment in which a PC is operated.

In step S12, the line of sight information measured in step S11 is evaluated. For instance, the distribution of transmission points is analyzed for the subject who is operating a PC and his gaze point is at the monitor. Using the analyzed distribution of the transmission points, various evaluations are made. For instance, evaluation is made as to which region on the spectacle lens is used when the subject gazes at the monitor, how far the monitor is from the eyeball, what a relationship is between the distance of the monitor from the eyeball and addition, what a relationship is between the size of the characters displayed on the monitor the subject gazes at and the amount of astigmatism at the transmission point. Similarly, the line of sight information when the subject gazes at the keyboard or a document used during the operation of the PC are also evaluated.

In step S13, a new progressive power spectacle lens is designed based on the result of evaluation obtained in step S12. Assume that a problem is to design, for instance, a progressive power spectacle lens that is more suited for the operation of a PC. In this case, further assume that the result of the evaluation in step S12 indicates that the subject uses only a region of the spectacle lens that has an amount of astigmatism of 0.5D or less when he gazes at the characters displayed on the monitor while he uses also a region of the spectacle lens that has an amount of astigmatism of up to 1.5D when he gazes at the keyboard. Then, a target for design may be decided as follows. For the region of addition that corresponds to the distance of the eyeball to the monitor, the amount of astigmatism is set at a reduced level of 0.5D or less and for the region of addition that corresponds to the distance of the eyeball to the keyboard, the amount of astigmatism of up to 1.5D is allowed. Thus a new progressive power spectacle lens can be designed according to this target.

The design method explained above is exemplary and the present invention is not limited to the above-mentioned design method. For instance, a target for more versatile design may be established by increasing the number of subjects or increasing the number of types of measurement environments.

Manufacture and Sales of Progressive Power Spectacle Lens

Figure 8:
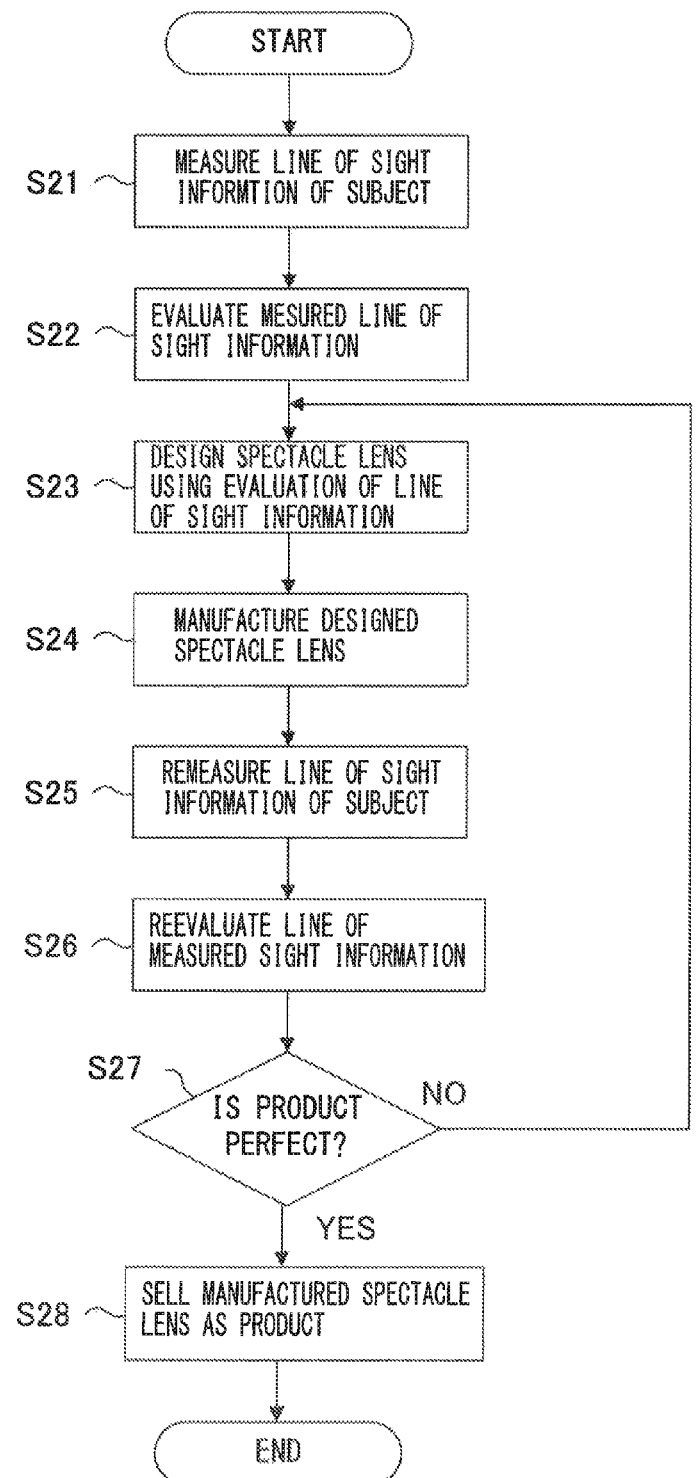
FIG. 8 is a flowchart illustrating a procedure of manufacture and sales of spectacle lenses.

Next, the procedure of manufacturing the new progressive power spectacle lens designed by using the result of measurement by the line of sight detection device 1 and distributing the product is explained referring to the flowchart illustrated in FIG. 8.

In FIG. 8, the procedure of measuring the line of sight information of the subject and evaluating the result in steps S21 to S23 and designing a progressive power spectacle lens using the result of the evaluation is the same as the procedure in steps S11 to S13 in FIG. 7 and detailed description of it is omitted.

Then, in step S24, the new progressive power spectacle lens designed in step S23 is manufactured. In step S25, the line of sight information of the subject wearing the new progressive power spectacle lens manufactured in step S24 is measured again in the same manner as in step S21. The result is evaluated again in step S26. In step S27, whether the new progressive power spectacle lens is perfect as a product is determined by, for instance, checking predetermined target performance. If the lens is perfect, the control proceeds to step S28. If the lens is imperfect, the control returns to step S23.

In the step S23 to which the control returned, the last design in step S23 is modified reflecting the result of evaluation in step S26 to perform redesign. Steps S24 to S26 are repeated again and the result is judged again in step S27. The procedure in steps S23 to S27 is repeated in any desired times to increase perfectness of the new progressive power spectacle lens. Then, the degree of perfection reaches a predetermined degree, a positive judgment is made in step S27 and the control proceeds to S28. The new progressive power spectacle lens is put on the market as a product.

The first embodiment explained above provides the following operations and advantageous effects.

(1) The line of sight detection device 1 includes a measurement means that measures the movement of an eyeball of a subject 3 wearing eyeglasses 2 (i.e., an eyeball camera 11 and an image processing device 17); a calibration computation device 18 that detects a gaze point in a forward field of view of the subject 3 based on the result of measurement by the measurement means; a calibration computation device 18 that detects a transmission point, at which a line of sight of the subject 3 toward the gaze point passes through the lens of the eyeglasses 2 based on the result of measurement by the measurement means; and a PC 16 that causes a gaze point mark 24 that indicates the position of the gaze point to be displayed at a monitor 19 in superimposition on a moving image 21 of the forward field of view and causes a left transmission point mark 25 and a right transmission point mark 26 that indicate the positions of the transmission points to be displayed in superimposition on a left lens image 22 and a right lens image 23, respectively, that represent the lens of the eyeglasses 2. This enables comprehensibly displaying interrelation between the position of the gaze point subject gazes at and the position of transmission point on the spectacle lens. That is, the result of detection of the gaze point and transmission point can be displayed in a useful manner upon design and selection of the spectacle lens. This display method is useful particularly for design and selection of progressive power spectacle lenses that have different refractive power in different regions.

(2) The line of sight detection device 1 described in (1) above is configured to display, in the second display method, a gaze point mark and left and right transmission point marks in superimposition and to display a moving image of the forward field of view and left and right lens images in superimposition. This enables comprehensible display of the relationship between the range of vision through the lens of the eyeglasses 2 of the subject 3 and the transmission point of the lens of the eyeglasses 2.

Second Embodiment

Referring to the drawings, a second embodiment of the present invention is explained. The second embodiment is featured by generation of a line of sight measurement report that assembles the gaze position data and transmission position data measured as mentioned above and thus explanation is focused on this point.

The PC 16 generates the line of sight measurement report described later based on the image of forward field of view inputted from the image processing device 17 and the gaze position data and the transmission position data outputted from the calibration computation device 18, displays the generated line of sight measurement report on the monitor 19, records the report at a recording medium such as a HD, which is not shown in the drawings, or outputs the report to the printer 20. The printer 20 prints the line of sight measurement report inputted from the PC 16 on paper to generate a line of sight measurement report on paper.

Figure 9:
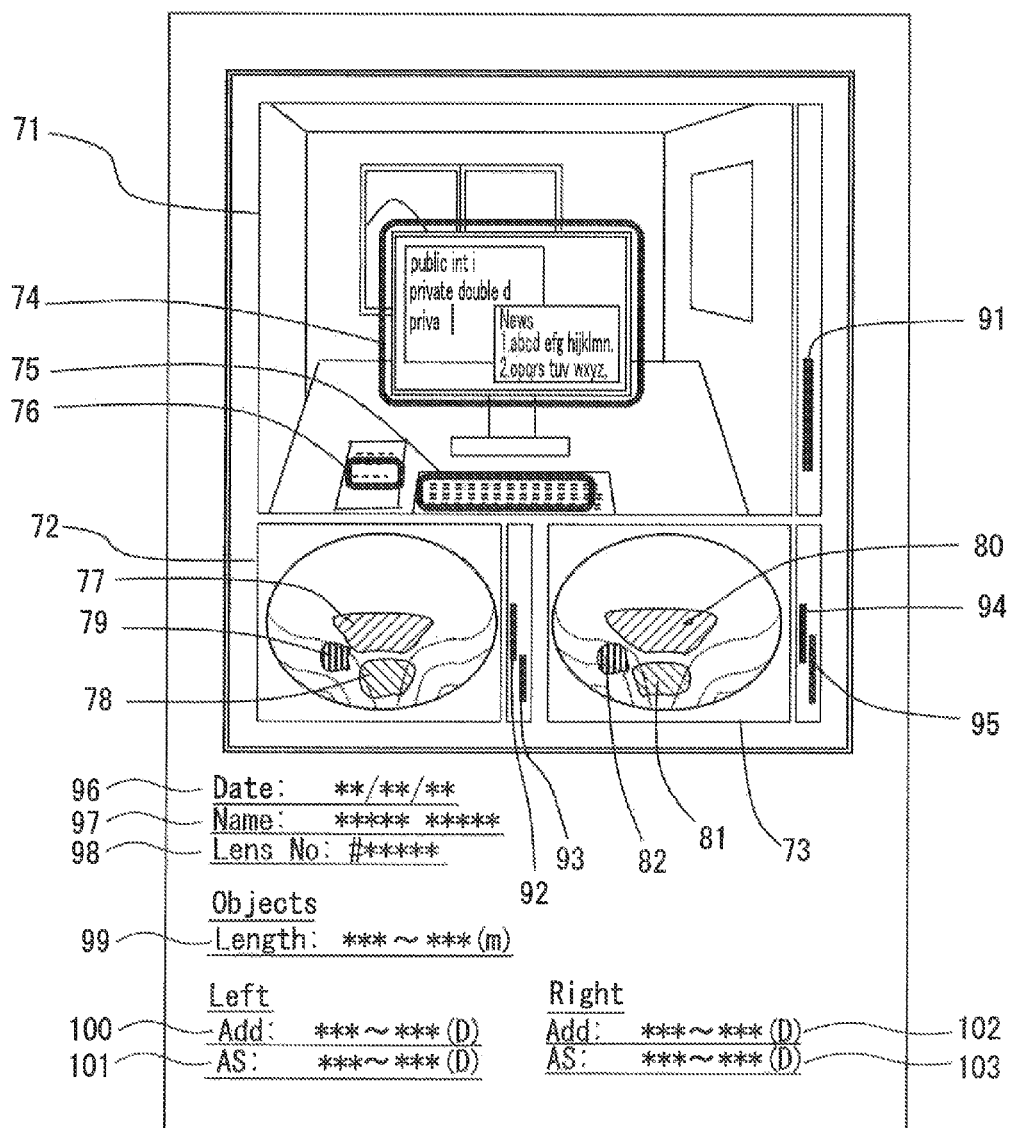
FIG. 9 is a diagram illustrating an example of a line of sight measurement report in a second embodiment according to the present invention.

FIG. 9 is a diagram showing an example of the line of sight measurement report. The line of sight measurement report shown in FIG. 9 assembles the data measured by the line of sight detection device 1 that measures the line of sight of the subject 3 in the conditions in which the subject is inputting a sentence written in a notepad into a PC through the keyboard. The line of sight measurement report contains transmission points at the left and right spectacle lenses plotted separately according to the range of gaze (for instance, monitor, keyboard, or notepad). Upon determining a transmission point for the range of gaze being a monitor, the PC 16 determines the range of the monitor using a conventional image processing method, such as a feature point extraction method from the image of the forward field of view. Then, the PC 16 compares the gaze position data with the coordinates of the range of the monitor to determine that the gaze point is within the range of the monitor, and determines the transmission point that corresponds to the gaze point. For the range of gaze being a keyboard or a notepad, the corresponding transmission point can be determined similarly.

Concretely, an image 71 of the forward field of view of the subject 3 is displayed above the line of sight measurement report and downside of the image 71 are displayed a left lens image 72 and a right lens image 73 side by side.

The image 71 of the forward field of view is a typical frame image extracted from the moving image captured by the forward field of view camera 10. The image 71 of the forward field of view includes the monitor and keyboard of the PC on the desk and a notepad on the side of the keyboard. On the image 71 of the forward field of view are displayed in superimposition a frame line 74 that surrounds the monitor and a frame line 75 that surrounds the keyboard, and a frame line 76 that surrounds a portion of the note pad.

The left lens image 72 and the right lens image 73 are images having a lens frame in which contour lines indicating the distribution of astigmatism at the lens are depicted. On the left lens image 72, a pattern 77 is displayed in superimposition. The pattern 77 shows a region occupied by a plurality of transmission points of the left side lens being plotted for the subject 3 who gazes at the range of the forward field of view that corresponds to the inside of the frame line 74 (i.e., monitor). Similarly, on the left lens image 72, a pattern 78 indicating the transmission region of the left side lens when the subject 3 gazes at the region of the forward field of view that corresponds to the inside of the frame line 75 (i.e., keyboard) and a pattern 79 indicating the transmission region of the left side lens when the subject 3 gazes at the region of the forward field of view that corresponds to the inside of the frame 76 (i.e., notepad) are displayed in superimposition.

On the right lens image 73, a pattern 80 indicating the transmission region of the right side lens when the subject 3 gazes at the region of the forward field of view that corresponds to the inside of the frame line 74 (i.e., monitor), a pattern 81 indicating the transmission region of the right side lens when the subject 3 gazes at the region of the forward field of view that corresponds to the inside of the frame line 75, and a pattern 82 indicating the transmission region of the right side lens when the subject 3 gazes at the region of the forward field of view that corresponds to the inside of the frame line 76 (i.e., notepad) are displayed in superimposition.

These displays enable the correspondence between the target object of gaze and the distribution of transmission points on the spectacle lens to be displayed obviously apparent at a glance. For instance, the region where the line of sight of the subject 3 passes through the eyeglasses 2 when the subject gazes the region of the forward field of view that corresponds to the inside of the frame line 74 (i.e., monitor) is the regions indicated by the patterns 77 and 80 overwritten on the left lens image 72 and the right lens image 73, respectively. The frame lines 74 to 76 depicted on the image 71 of the forward field of view and the patterns 77 to 82 depicted on the left lens image 72 and the right lens image 73 are supposed to be distinguishably displayed with respect to the correspondence by using labels or colors.

On the right side of the image 71 of the forward field of view, a bar graph 91 is displayed, which indicates the ranges of distance of the gaze point from the eyeball of the subject 3 when the subject 3 gazes at the regions of the forward field of view that correspond to the frame lines 74, 75, and 76.

Further, on the right side of the left lens image 72, a bar graph 92 indicating the range of addition at the transmission point of the left side lens when the subject gazes at the regions of the forward field of view that correspond to the frame lines 74, 75, and 76 and a bar graph 93 indicating the range of the amount of astigmatism at the transmission point are displayed side by side. The bar graph 92 indicates the range of addition in the regions indicated by the patterns 77, 78, and 79 on the left side lens and the bar graph 93 indicates the range of the amount of astigmatism in such regions.

Similarly, on the right side of the right lens image 73, a bar graph 94 indicating the range of addition at the transmission point of the right side lens when the subject 3 gazes at the regions of the forward field of view that corresponds to the frame lines 74, 75 and 76 and a bar graph 95 indicating the range of the amount of astigmatism at the transmission point are displayed side by side. The bar graph 94 indicates the range of addition in the regions that the patterns 80, 81 and 82 on the right side lens indicate and the bar graph 95 indicates the range of the amount of astigmatism in such regions.

The bar graphs 91 to 95 in FIG. 9 are prepared as indicating the ranges of values of the amount of astigmatism when the subject gazes at the three regions that correspond to the frame lines 74, 75 and 76. However, the present invention is not limited to this. For instance, they may be prepared as indicating the amount of astigmatism when the subject gazes at any designated one of the three regions corresponding to the frame lines 74, 75, and 76. For instance, they may be displayed as a plurality of divided bar graphs corresponding to the frame lines 74, 75, and 76 in different colors, respectively.

Downside of the left lens image 72 and the right lens image 73 are displayed the measurement date 96, the name 97 of the subject 3, the identification number 98 of the eyeglasses 2, and the numerical values 99 to 103 the bar graphs 91 to 95 represent. In FIG. 9, the characters and numeric characters are replaced by asterisk mark (*) for the data.

Figure 10:
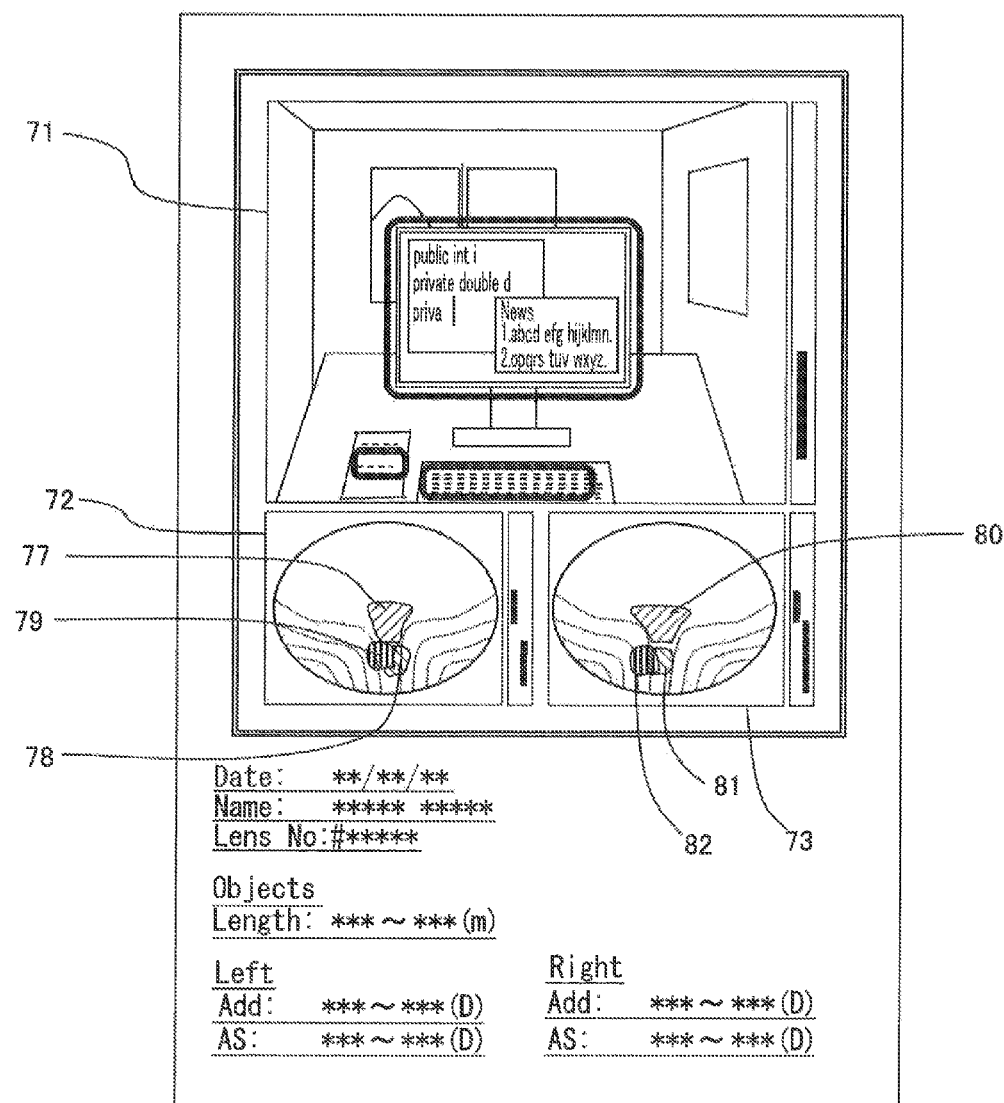
FIG. 10 is a diagram illustrating an example of a line of sight measurement report in the second embodiment.

FIG. 10 shows an example of the line of sight measurement report for the same subject 3 wearing eyeglasses different than the eyeglasses used in the measurement illustrated in FIG. 9. Comparison of FIG. 9 with FIG. 10 confirms that patterns 77 to 81 indicating the transmission regions of the spectacle lens are more concentrated in the central part of the spectacle lens in FIG. 10 than in FIG. 9. This means that the use of the spectacle lens is limited to its smaller central part when the subject 3 wears the eyeglasses used in the measurement illustrated in FIG. 10 than the central part of the eyeglasses used in the measurement illustrated in FIG. 9. In other words, the subject 3 is supposed to move the line of sight by turning his head since he can gaze at the target object only through the central part of the spectacle lens in the measurement shown in FIG. 10. Assume that the eyeglasses that enable change of the line of sight without so much movement of the head of the wearer are defined to be good eyeglasses. Then, the eyeglasses used in the measurement of FIG. 9 are suggested to be better eyeglasses than the eyeglasses used in the measurement of FIG. 10.

The line of sight measurement report, which is information manifesting whether the spectacle lens fits the subject 3 as just described, thus allows a measurer, i.e. a person who measures to use it when he explains the result of measurement to the subject 3. At eyeglasses shops, use of the line of sight measurement report enables selection of the best fitting progressive power spectacle lens to the subject, who plans to purchase some, from a plurality of progressive power spectacle lenses having different characteristics from each other.

Figure 11:
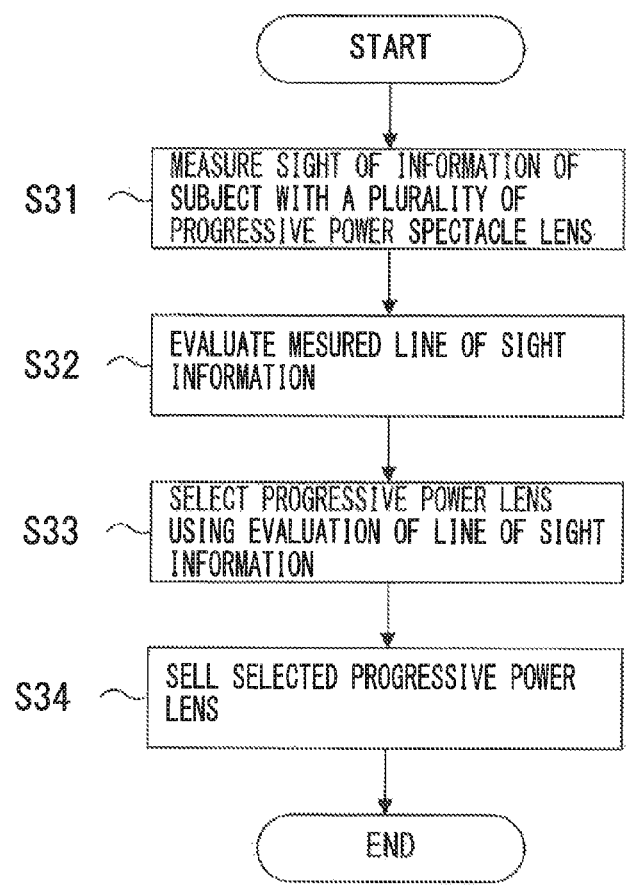
FIG. 11 is a flowchart illustrating a procedure of selecting spectacle lenses.

The procedure of selecting the best fit progressive power spectacle lenses is explained referring to the flowchart illustrated in FIG. 11. In step S31, a plurality of, e.g., three progressive power spectacle lenses are provided as options. The line of sight detection device 1 measures the line of sight information of the subject for each spectacle lens when he wears it. The three progressive power spectacle lenses differ in characteristics from each other. For instance, one of them is the progressive power spectacle lens the subject now uses and the other two are trial lenses, which are new candidate eyeglasses for purchase. The measurement of the line of sight information is performed in the same manner as that in step S11 of FIG. 7 and the line of sight measurement report is prepared by the PC 16 for each of the measured progressive power spectacle lenses and is printed by the printer 20. The environment in which the subject is placed is the same for all the measurements.

In step S32, the line of sight information measured in step S31 is evaluated. For instance, which one of the three progressive power spectacle lenses has the widest distribution of transmission position data is evaluated. The subject can compare the line of sight measurement reports on the results of measurements using the three progressive power spectacle lenses with each other to perform objective evaluations on whether they fit to him when he wears them. Consequently, use of the line of sight measurement reports enables the measurer to explain the characteristics of the three progressive power spectacle lenses to the subject comprehensibly.

In step S33, one progressive power spectacle lens is selected from the three progressive power spectacle lenses based on the result of evaluation in step S32. If, for instance, a progressive power spectacle lens that allows use of the widest region of the progressive power spectacle lens is deemed to be good, one having the widest distribution of the transmission position data may be selected from the three progressive power spectacle lenses. Although the above example explains the selection of only one progressive power spectacle lens, a plurality of progressive power spectacle lenses may be selected.

In step S34, the eyeglasses shop may sell the progressive power spectacle lens selected in step S33 to the subject.

As stated above, when the subject intends to purchase new eyeglasses at an eyeglasses shop, the line of sight detection device 1 measures his line of sight in a condition in which he wears the eyeglasses he is now using and one or more conditions in which he wears one or more new spectacle lenses to prepare line of sight measurement reports. This enables comparison of the transmission region of the eyeglasses now in use with that of new eyeglasses using the line of sight measurement reports and thus helps select new eyeglasses.

Another form of the line of sight measurement report may be a sheet of paper that assembles the results of measurements obtained with a plurality of pairs of eyeglasses including new and old ones. For simplification, the image 71 of the forward field of view may be omitted and only the left lens image 72 and the right lens image 73 at a plurality of pairs of eyeglasses, on which images patterns 77 to 82 showing at least one transmission region is displayed in superimposition, may be printed side by side.

Another use of the line of sight measurement report is a material for sales promotion for a newly developed spectacle lens. The line of sight of the same subject wearing each of the spectacle lenses of a plurality of new and old designs is measured by the line of sight detection device 1 and line of sight measurement reports pare prepared and printed as pamphlets or posters, which may serve as materials for sales promotion.

The above explained second embodiment has the following operations and advantageous effects. In the line of sight measurement report, the frame lines 74 to 76 indicating the position of gaze points are printed on the image 71 of the forward field of view in superimposition and the patterns 77 to 82 indicating the position of the transmission points are printed on the left lens image 72 and the right lens image 73. This helps the measurer explain the relationship between the target object to be gazed and the distribution of the transmission points on the spectacle lens to the subject's recognition. Consequently, a spectacle lens that fits the subject 3 can be selected and sold with ease using the line of sight measurement report.

Variation Example 1

Figure 12:
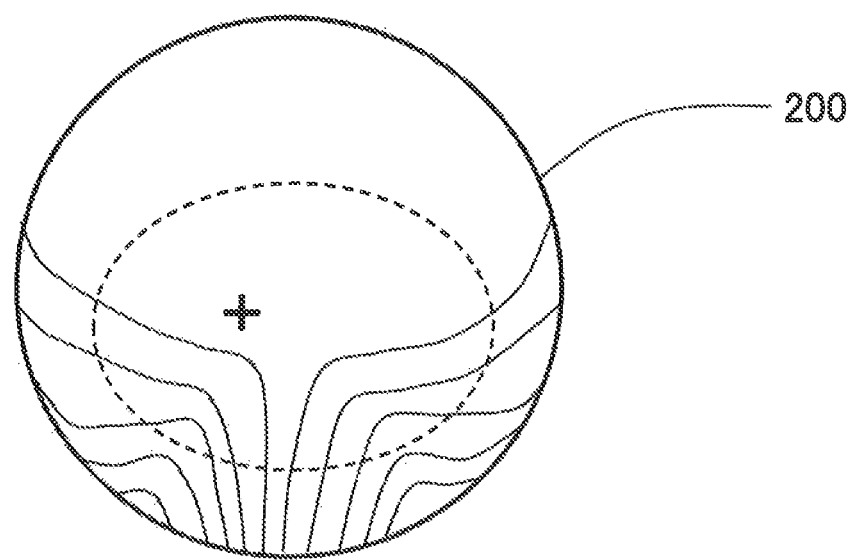
FIG. 12 is a diagram illustrating an example of display of a lens image in Variation Example 1.

In the first and second embodiments described above, examples are explained in which the left lens image and the right lens image are displayed along the shape of the frame of the eyeglasses. However, the present invention is not limited to this. For instance, the lens images may be displayed along the shape 200, which is the shape of the lens before rounding as shown in FIG. 12.

Variation Example 2

Figure 13:
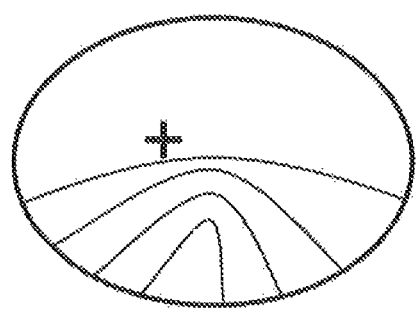
FIG. 13 is a diagram illustrating an example of display of a lens image in Variation Example 2.

In the first and second embodiments described above, examples are explained in which the left lens image and the right lens image are displayed as aberration maps that indicate the distribution of astigmatism in level lines. However, the present invention is not limited to this. For instance, the lens images may be displayed as addition maps that indicate the distribution of addition of the lens or a diagram that indicates the reference point for distant vision and the reference point for near vision, or a diagram that indicates only the shape of frame as shown in FIG. 13. For instance, the lens images may be images captured by the eyeball imaging camera 11.

Variation Example 3

In the left lens image and the right lens image, the region of transmission points which is recommendable for lens design simulated based on the distance of the eyeball to the gaze point may be displayed in a different color than the colors of the rest.

Variation Example 4

In the first embodiment, the example is explained in which marks representing the position of the gaze point and the transmission point are displayed. However, the present invention is not limited to this. For instance, the position of the gaze point and the transmission point may be displayed as a stationary point frequency map or a trajectory.

Variation Example 5

In the first embodiment, the example is explained in which the gaze point and the position of transmission point during the measurement by the line of sight detection device 1 are displayed. However, for instance, the positions of the gaze point and of the position of transmission point measured in the past by the line of sight detection device 1 or the gaze point and the position of transmission point of any other subject measured as a target for comparison may be displayed in superimposition on the moving image of the forward field of view or on the left and right lens images. In addition, statistical data of the positions of gaze point and/or of transmission point measured for a plurality of subjects may be gathered to calculate an average position of the gaze points and/or of transmission points and the calculated average position may be displayed on the moving image of the forward field of view or on the left and right lens images in superimposition.

In the first embodiment, the PC 16 may be configured to cause the moving image of the forward field of view to be omitted and to cause only the left and right lens images, on which the position of at least one transmission point (i.e., transmission region) measured by the line of sight detection device 1 is displayed in superimposition, to be displayed on the monitor 19. In this case, the PC 16 may be configured to cause both the position of the transmission point which is currently measured and the position of the transmission point measured for the same subject in the past to be displayed on the left and right lens images in superimposition.

Variation Example 6

In the above embodiment, the example in which use is made of the line of sight detection device 1 of the type which is put on the head of subject 3 as shown in FIG. 1 is explained. However, the present invention is not limited to this. The line of sight detection device 1, which is only needed to have a function of measuring relative movement of the eyeball of the subject 3 with respect to his head, may be, for instance, a stationary line of sight detection device combined with another device that detects the movement of the head.

Variation Example 7

In the above embodiment, the example in which the position of the transmission point is displayed on the lens images in superimposition is explained. However, the position of the transmission point may be displayed on the two-dimensional coordinates.

Third Embodiment

Figure 14:
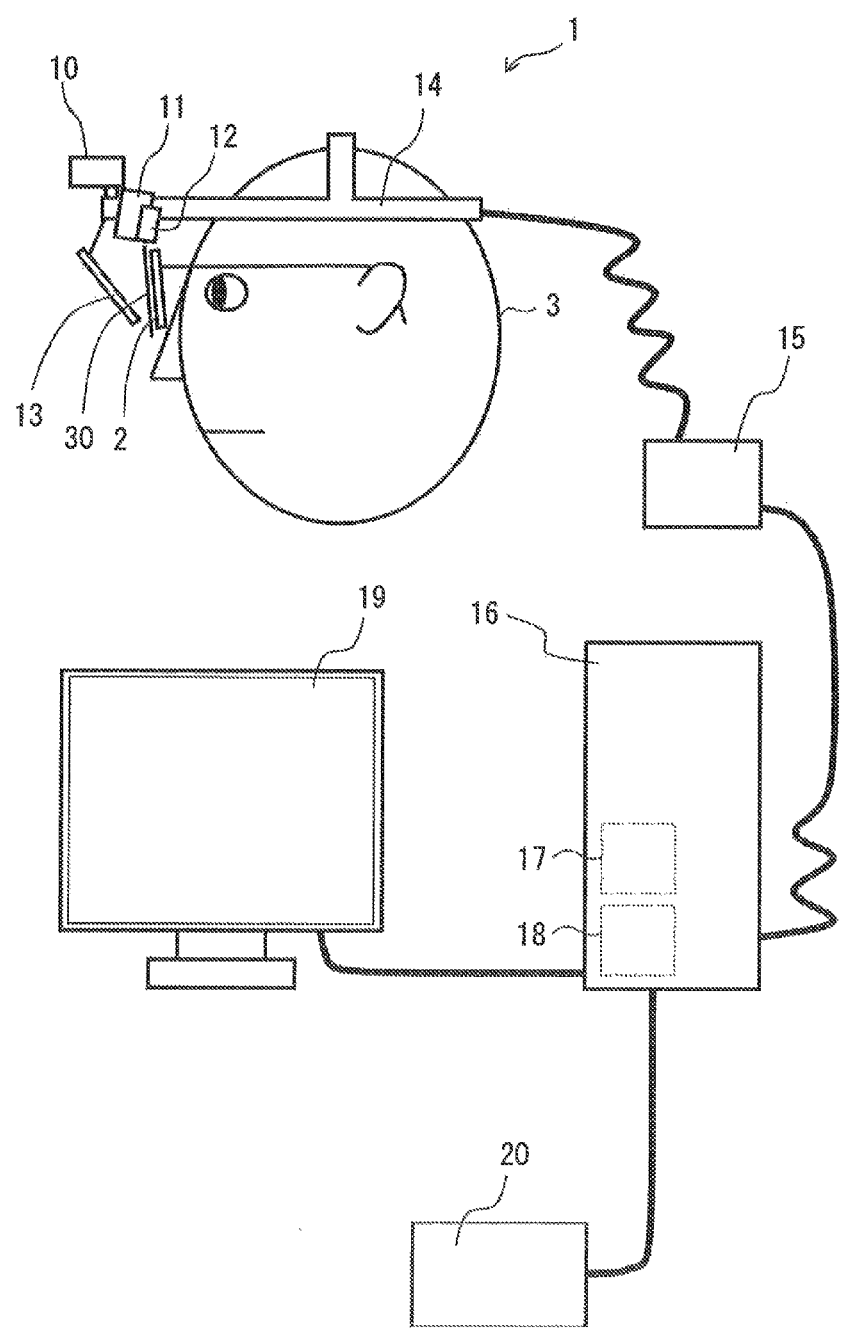
FIG. 14 is a diagram illustrating the construction of a line of sight detection device according to a third embodiment of the present invention.

A third embodiment according to the present invention is explained referring to the attached drawings. FIG. 14 is a diagram illustrating the construction of the line of sight detection device 1 according to a third embodiment of the present invention. In FIG. 14, the line of sight detection device 1 detects the line of sight of the subject 3 wearing the eyeglasses 2. Upon any calibration described later, a reference board 30 described later is attached to the outer peripheral part of the lens of the eyeglasses 2.

FIG. 14 is the same as FIG. 1 except for the reference board 30. Thus the same reference numbers are allotted to the same or like components and their explanation are omitted.

The coordinates of any transmission point are coordinates on the lens surface of the eyeglasses 2 as explained in the first embodiment. The surface at which the transmission point is measured may be either the front surface or the rear surface of the lens of the eyeglasses 2. For any aspheric lens, in particular any progressive power lens, a reference surface in the design of such lens may be used. This is more advantageous for design than any other surfaces. For any lens of the eyeglasses 2 that is a progressive power lens, the progressive power surface of which is its rear surface, the coordinates of the transmission point measured at the front surface can be approximately converted into the coordinates of the transmission point at the rear surface reflecting the angle of line of sight and the refractive mark of the lens of the eyeglasses 2.

Now, the relationship between the eyeball movement data and the gaze position data and the calibration method of calibrating the relationship between the eyeball movement data and the transmission position data are explained below. The central coordinates of the pupil and cornea reflection, which constitute the eyeball movement data, are converted into the coordinates of the gaze point, which constitute the gaze position data, and the coordinates of the transmission point on the lens of the eyeglasses 2, which constitute the transmission position data with mathematical formula or expression having a plurality of coefficients, respectively. The conversion formula may be a single formula that expresses the horizontal coordinate and the vertical coordinate of the gaze point and the transmission point or a plurality of formulas corresponding to several regions divided depending on the gaze point and the transmission point. In the latter case, preferably, the individual formulas are smoothly connected to each other at their boundaries. The division of regions may be finer as the distribution of refractive power of the progressive power lens is more characteristic. These conversion formulas are formed to have sufficient flexibility to cope with complexity of conversion for any lens of the eyeglasses 2 that has a characteristic distribution of refractive power, such as a progressive power lens.

If the lens of the eyeglasses 2 is a simple monofocal spherical lens, the shift or difference between the position of the transmission point on the lens of the eyeglasses 2 and the attainment or mark of the line of sight due to refraction is a nonlinear relationship to be expressed by a cubic (third order) or higher equation. For a range in which the line of sight is measured is a field of view as wide as around ±30 degrees or further ±45 degrees, such relation is expressed by an equation of much higher order. For a progressive power lens, such relation is rotation asymmetric and more complicated. That is, to more precisely express the deviation of line of sight due to the refraction of the eyeglasses, a third order or higher equation is needed for a range having a field of view of narrower than ±30 degrees and an at least fourth order equation is needed for a range having a field of view of wider than ±30 degrees.

$$X = A_{44}x^4y^4 + A_{43}x^4y^3 + A_{34}x^3y^4 + \ldots + A_{11}xy + A_{01}y + A_{10}x + A_{00} \quad (1)$$

$$Y = B_{44}x^4y^4 + B_{43}x^4y^3 + B_{34}x^3y^4 + \ldots + B_{11}xy + B_{01}y + B_{10}x + B_{00} \quad (2)$$

$$X' = A_{44}'x^4y^4 + A_{43}'x^4y^3 + A_{34}'x^3y^4 + \ldots + A_{11}'xy + A_{01}'y + A_{10}'x + A_{00}' \quad (3)$$

$$Y' = B_{44}'x^4y^4 + B_{43}'x^4y^3 + B_{34}'x^3y^4 + \ldots + B_{11}'xy + B_{01}'y + B_{10}'x + B_{00}' \quad (4)$$

The formulas (1) and (2) above are conversion formulas for converting the eyeball movement data into the gaze position data. In the formulas (1) and (2), X and Y are coordinates of the gaze point. x and y are values of differences in the central coordinates between the pupil and the cornea reflection. The formulas (3) and (4) are conversion formulas for converting the eyeball movement data into the transmission position data. In the formulas (3) and (4), X' and Y' are coordinates of the transmission point and x and y are values of differences in the central coordinates between the pupil and the cornea reflection.

The coefficients in the formulas (1) to (4) are actually measured and calibrated for each subject 3, preferably for each measurement. This calibration enables correction of, for instance, the deviation or difference caused by the condition of attachment of the line of sight detection device 1 to the head of the subject 3, an interindividual difference of the shape of the eyeball of the subject 3, the deviation of the line of sight due to refraction at the lens of the eyeglasses 2, the distortion of the image of eyeball due to refraction at the lens of the eyeglasses 2, the distortion of the field of view due to the aberration of the forward field of view camera 10, and the aberration due to the difference in position between the left and right eyes and the forward field of view camera 10.

Calibration of Gaze Position Data

Upon calibration of the relationship between the eyeball movement data and the gaze position data, the subject 3 gazes at a plurality of stationary marks of which the position with respect to the subject 3 is known. Subsequently, the coefficients of the formulas (1) and (2) are determined based on the then obtained eyeball movement data by the calibration computation device 18 using a least-square method to make the position of the gaze point calculated according to the formulas (1) and (2) match the position of the marks.

Figure 15:
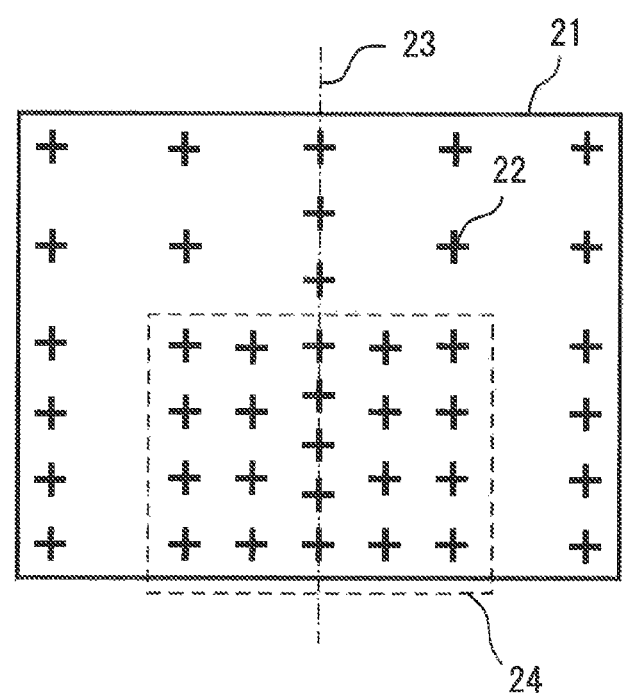
FIG. 15 is a diagram illustrating an example of the layout of marks.

FIG. 15 shows an example of layout of the marks for calibration. A mark 22 is printed on a mark plate 21. The mark plate 21 is placed at a distance of, for instance, 2 m from the subject 3 and disposed in the direction toward the center of the field of view of the subject 3 and in such a manner that the mark plate 21 in whole is within the field of view of the forward field of view camera 10. The mark 22 is arranged in a range of an angle of field of view at least in the horizontal direction of greater than 60 degrees and preferably, so as to cover substantially all the range of the field of view the subject 3 can see using the eyeglasses 2, The mark 22 is arranged at a higher density in a region of the lens of the eyeglasses 2 exhibiting a greater change in refractive power.

The marks 22 are arranged at least 5 points in each of the vertical direction (Y direction) and the horizontal direction (X direction) in total at least 25 points. This enables determination of all the coefficients of the fourth order formulas in the equations (1) and (2) by the least square method.

Specifically, this is done as follows. For instance, for any eyeglasses 2 having progressive power lenses, the marks 22 are arranged in a range of an angle of field of view in the horizontal direction of ±45 degrees and angles of field of view in the vertical direction of within 30 degrees upwards and of within 45 degrees downwards. The marks 22 are arranged in high densities on the a vertical line 23 that passes through the center of the field of view of the subject 3 and in a region 24 that is lower than the center. The vertical line 23 corresponds to the principal meridian of the progressive power lens of the eyeglasses 2. The region 24 lower than the center corresponds to the progressive power part between the region for reading and the region for near vision. A region in which the mark 22 is arranged at a higher density provides a more precise calibration coefficient determined by the least square method and allows verification. This enables efficient and high precision calibration computation of eyeglasses if the eyeglasses have a characteristic distribution of refractive power, such as progressive power lenses.

Any progressive power lens has a region in which the distribution of refractive power manifests a characteristic change, which region ranges over a distance of about 20 mm from the center of the lens downward on the principal line. In this range, the addition of the lens changes by at most about 4 diopters. Thus, arranging four or more marks in the region 24 that corresponds to the progressive power part region will result in a denser arrangement of the mark 22 than a pitch of 1 diopter, which enables calibration and verification with sufficient precision. This also enables reduction in precision of the calibration of the lens, in particular the progressive power part to 2 degrees or lower in terms of angle of line of sight. The angle of line of sight of 2 degrees or lower is converted to about 1 mm in the coordinates of the lens of the eyeglasses 2. The precision of 1 mm is sufficient since the specifications such as progressive zone length and amount of inset are designed on the order of mm.

Upon measurement of the gaze point data for calibration, measurement may be performed using any one of the marks 22 on the mark plate 21. Therefore, the part for which a higher precision of calibration is desired is measured using more marks 22. All the marks 22 have respective labels and the actually used label is notified to the calibration computation device 18 via the PC 16. The calibration computation device 18 identifies the mark 22 used in the measurement based on the notified label and calibrates the coefficients in the equations (1) and (2) using the data of the mark 22 that is used for measurement.

To calibrate the parallax due to a difference between the left and right eyes and the position of the forward field of view camera 10, it is necessary to place the mark plate 21 at a plurality of known positions, for instance, a position at a distance of 1 m or 0.2 m from the subject 3 in addition to the position at a distance of 2 m from the subject 3 and to perform measurement at each of the positions. In this case, it is sufficient to use the mark at a single position in the center of the field of view for the measurement.

Calibration of Transmission Position Data

Upon calibration of the relationship between the eyeball movement data and the transmission position data, the subject 3 gazes in a direction along which the line of sight passes through at a point on the lens of the eyeglasses 2 the position of which point is known. Based on the eyeball movement data thus measured, the calibration computation device 18 determines the coefficients of the equations (3) and (4) by the least square method so that the position of the transmission point calculated according to the equations (3) and (4) corresponds to the position of the known point.

Figure 16:
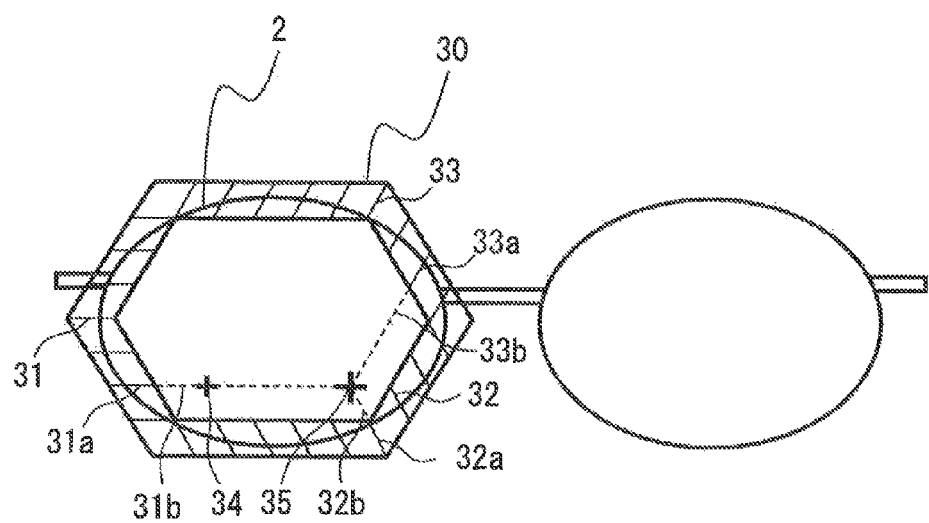
FIG. 16 is a diagram illustrating a reference board.

FIG. 16 is a diagram illustrating an example of the reference board 30 used upon calibration of the transmission position data. The reference board 30 has a hexagonal ring shape and is attached to the outer periphery of the eyeglasses 2. How to attach the reference board 30 is insignificant. Any method that allows removal of it can be used; for instance, a double-stick tape is used. The ring-shaped reference board 30, which is void in its inside, prevents no line of sight of the subject 3 and has no effects on the image capturing of the eyeball of the subject 3 by the eyeball imaging camera 12 of the line of sight detection device 1.

On the reference board 30 are depicted three types of baselines 31 to 33 extending in three different directions, with any two of them forming an angle of about 120 degrees. The respective types of baselines 31 to 33 in the three directions, each of which includes a plurality of baselines depicted at the same intervals in each of the three directions. On the lens of the eyeglasses 2 are impressed two marks 34 and 35 the positions of which on the lens are known, arranged side by side, for instance, in the horizontal direction. The reference board 30 is attached to the eyeglasses 2 in such a manner that lines 31b to 33b extending from predetermined baselines 31a to 33a, respectively, among the baselines 31 to 33, may form an intersection point that corresponds to the mark 35 and a line 31b extending from the baseline 31a passes the mark 34. This allows positioning of the baselines 31 to 33 with respect to the lens of the eyeglasses 2. The marks 34 and 35 used for the positioning of the baselines 31 to 33 may be impressed at at least two positions. The lines 31b to 33b in FIG. 16 are for illustration purposes and they are imaginary. In FIG. 16, use of the reference board 30 attached to only one of the lenses of the eyeglasses 2 is illustrated. Actually, however, the reference board 30 is attached to each of the lenses of the eyeglasses 2.

Figure 17:
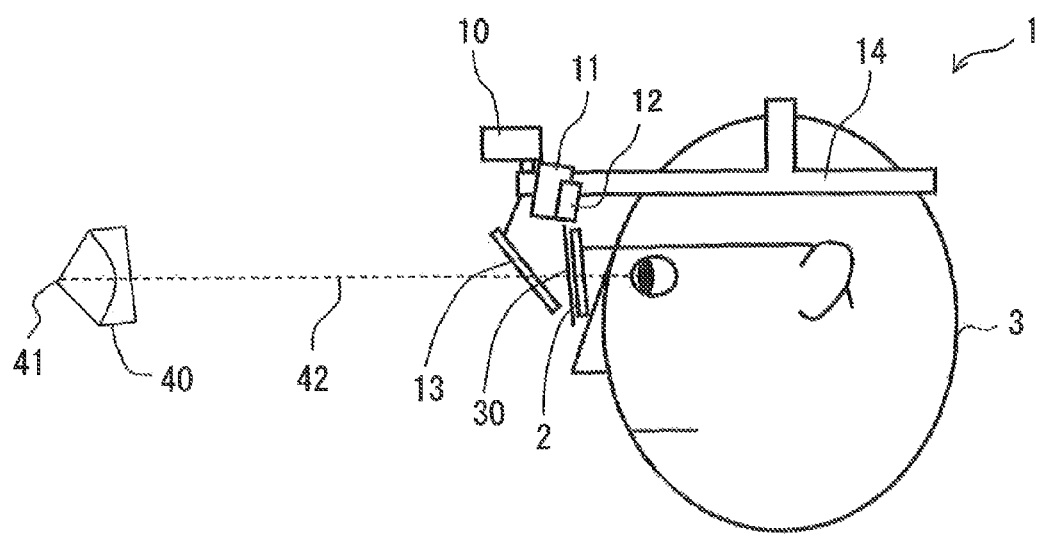
FIG. 17 is a diagram illustrating a method of measuring eyeball movement data upon calibration of transmission position data.

FIG. 17 illustrates the measurement method for measuring the eyeball movement data used when the transmission position data is calibrated. The subject 3 holds a corner cube 40 in his hand and gazes in a direction toward a top 41 at which the ridgelines of the corner cube 40 intersect with each other. Due to the characteristics of the corner cube 40, light that enters the corner cube 40 is reflected in a direction opposite to the direction of the incident light no matter which direction the corner cube 40 turns. Consequently, the subject 3, who gazes in the direction toward the corner cube 40, will observe his pupil reflected in the corner cube 40.

Figure 18:
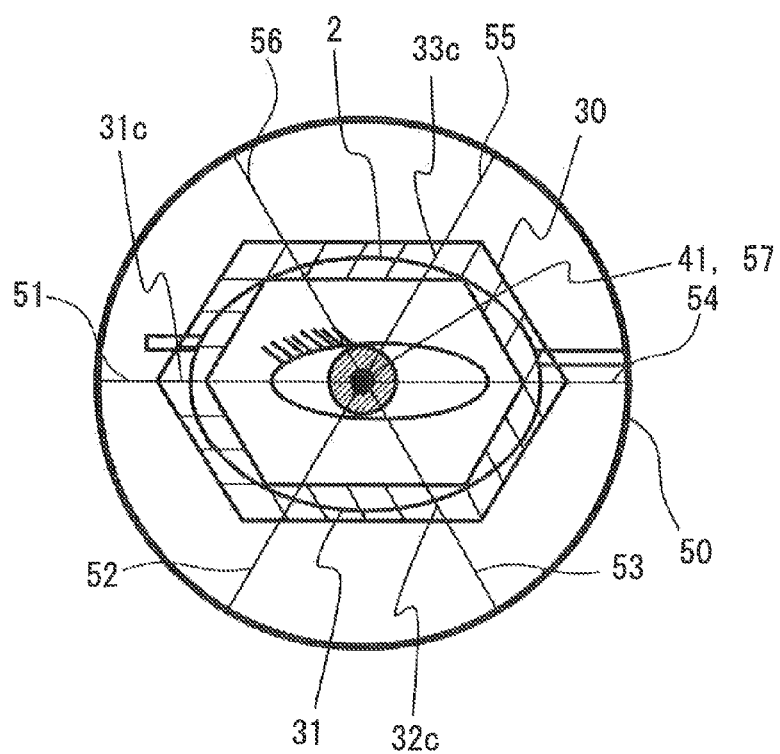
FIG. 18 is a diagram illustrating a field of view reflected in a corner cube.

FIG. 18 is a diagram illustrating the range of vision reflected by the corner cube 40 when the subject 3 gazes the top 41 of the corner cube 40. The subject 3 can observe, within the edge 50 of the corner cube 40, lines 51 to 56 consisting of three ridgelines of the corner cube 40 and three images of the ridgelines reflected at opposite surfaces of the corner cube 40. The top 41 is a point at which the lines 51 to 56 intersect with each other. If the subject 3 gazes in the direction toward the top 41, a pupil 57 of the subject 3 is reflected in superimposition at the top 41 of the corner cube 40 regardless of the direction of the corner cube 40 due to its characteristics. The subject 3 can readily recognize that the top 41 and the pupil 57 are in superimposition one on another although he can see the pupil 57 that is slightly blurred since the top 41 is focused on.

The subject 3 moves his hand or neck to adjust the positional relationship between the corner cube 40 and his head so that any three of the lines 51 to 56 consisting of three ridgelines of the corner cube 40 and three images of the ridgelines can be superimposed on the predetermined baselines 31c to 33c. The line of sight detection device 1 measures the eyeball movement data when the subject 3 gazes at the top 41 of the corner cube 40 in this adjusted condition. This means that the line of sight 42 (FIG. 17) of the subject 3 passes the intersection point of the lines extending from the baselines 31c to 33c at the lens of the eyeglasses 2. As mentioned above, the baselines 31 to 33 are positioned relative to the marks 34 to 35, the positions of which on the lens of the eyeglasses 2 are known, and thus the position of the above mentioned intersection point at the lens of the eyeglasses 2 can be determined from the positions of the marks 34 and 35.

Figure 19:
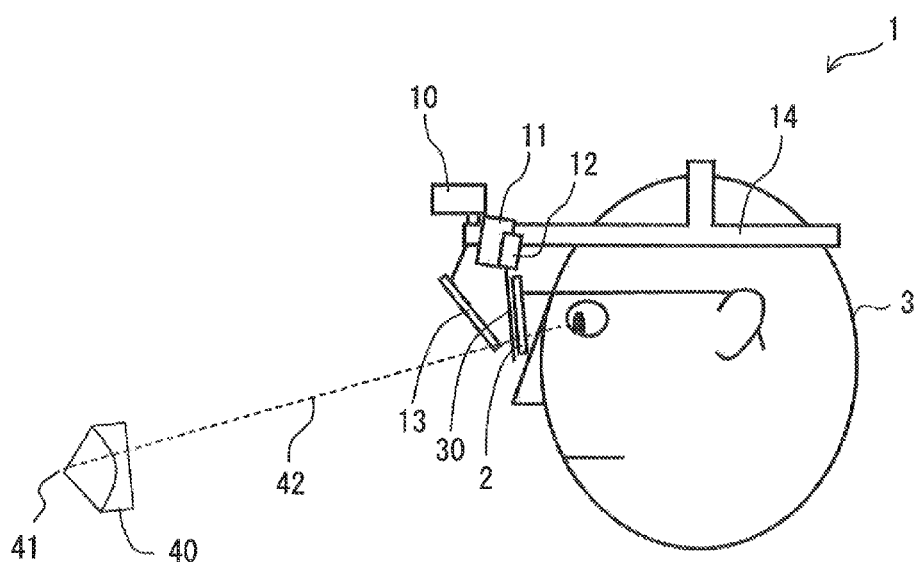
FIG. 19 is a diagram illustrating a method of measuring eyeball movement data upon calibration of data of transmission position.
Figure 20:
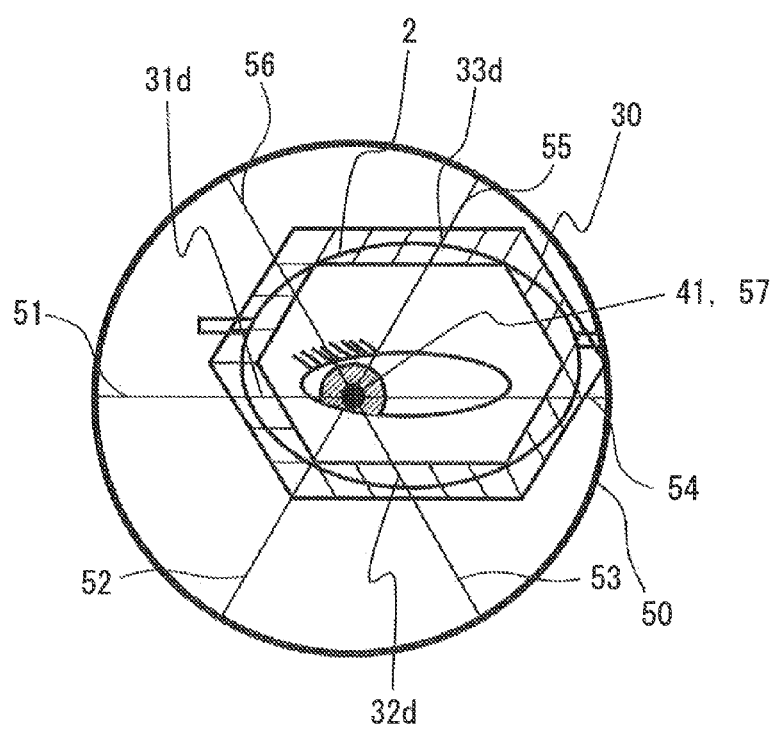
FIG. 20 is a diagram illustrating a field of view reflected in the corner cube.

Next, the subject 3 moves, for instance, his hand or neck to adjust the positional relationship between the corner cube 40 and his head and changes the position at which the line of sight 42 passes through the lens of the eyeglasses 2 from the condition shown in FIG. 17 to the condition shown in FIG. 19. On this occasion, the subject 3 further moves, for instance, his hand or neck to adjust the range of vision reflected by the corner cube 40 so that the any three of the lines 51 to 56 consisting of three ridgelines of the corner cube 40 and three images of the ridgelines are superimposed on the predetermined three baselines 31d to 33d among the baselines 31 to 33 at the reference board 30 as shown in FIG. 20. The line of sight detection device 1 measures and records the eyeball movement data when the subject 3 gazes at the top 41 of the corner cube 40 in this adjusted condition. This means that the line of sight 42 (FIG. 17) of the subject 3 passes the intersection point of the lines extending from the baselines 31d to 33d at the lens of the eyeglasses 2.

The measurement of the eyeball movement data at the transmission point determined by the set of the three baselines 31 to 33 is repeated for a plurality of transmission points (i.e., the plurality of sets of the baselines 31 to 33). The calibration computation device 18 calibrates the coefficients of the equations (3) and (4) based on the results of the measurements. The above-mentioned calibration is performed for each of the left and right eyes.

The equations (3) and (4) are expressed by third order or higher equations, preferably by fourth order or higher equations and thus the transmission points used for the measurement of the eyeball movement data are as many as 5 or more in each of the vertical direction (Y direction) and the horizontal direction (X direction) in total 25 or more depending on the largeness of the field of view. Upon calibration of the gaze point, the transmission points used for the measurement of the eyeball movement data need not be as many as the gaze points used for the measurement of the eyeball movement data (i.e., as the marks 22).

Figure 21A:
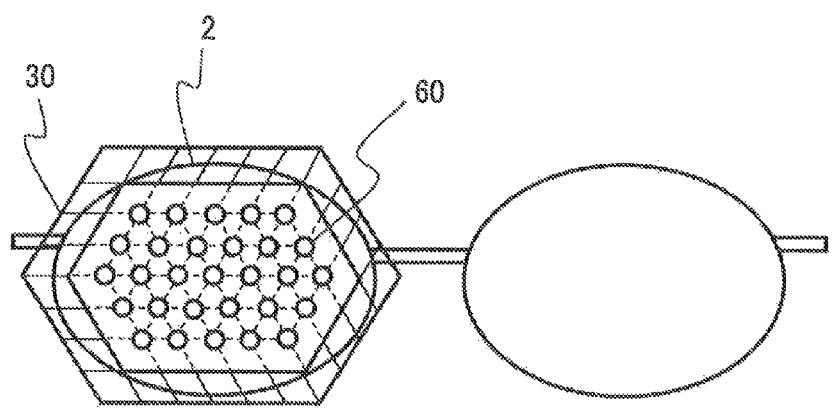
FIG. 21A-21C are diagrams illustrating examples of the layout of transmission points at which eyeball movement data is measured.
Figure 21B:
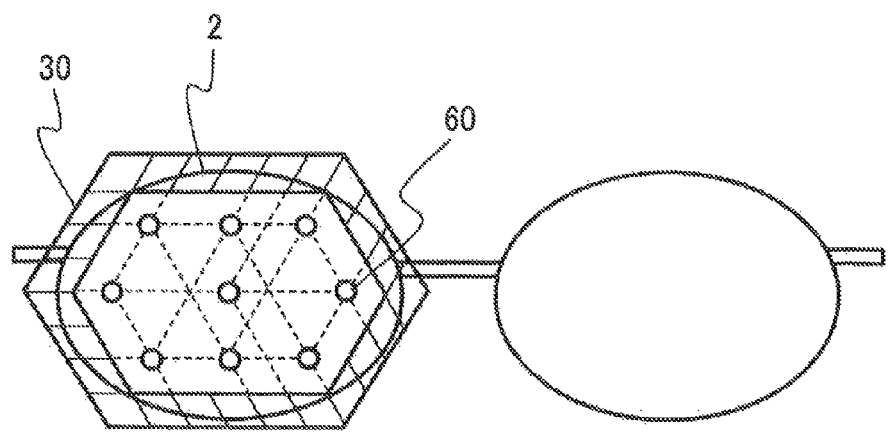
Figure 21C:
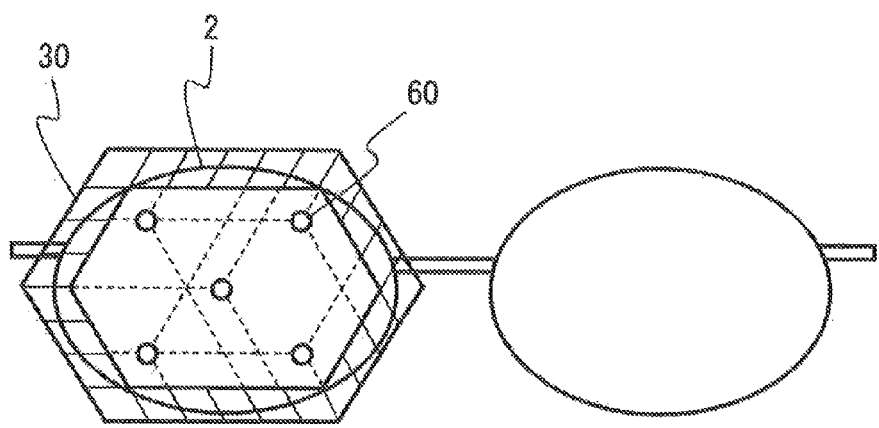

FIG. 21A-21C are diagrams illustrating examples of layout of the transmission points for the measurement of the eyeball movement data. The example of layout shown in FIG. 21A contains in total 29 transmission points 60 over a large range of the lens of the eyeglasses 2 and thus enables calibration of the coefficients of the fourth order equations (3) and (4). However, in case that reduction in precision of measurement is allowable and importance is given to simplicity, the number of the transmission points 60 to be used for the measurement of the eyeball movement data may be decreased as in the example of layout shown in FIG. 21B or FIG. 21C. In this case, the order of the equations (3) and (4) becomes lower.

In the measurement mentioned above, the two conditions need be satisfied simultaneously. The first one is that the top 41 of the corner cube 40 corresponds to the center of pupil 57 and the second one is that the lines 51 to 56, i.e., the ridgelines of the corner cube 40 and lines corresponding to the images of such ridges correspond to the baselines 31 to 33 of the reference board 30. However, due to the characteristics of the corner cube 40, the first condition is always satisfied regardless of the orientation of the corner cube 40. This avoids influences of blurring of images due to movement of the hand holding the corner cube 40 during the measurement and eliminates the need for finding the center of pupil 57. Consequently, reduction in time of measurement and improvement of precision of measurement can be achieved easily.

As described above, the relationship between the eyeball movement data of the subject 3 and the gaze position data and the relationship between the eyeball movement data of the subject 3 and the transmission position data are calibrated. This enables the line of sight detection device 1 to measure the gaze position data of the subject 3 with high precision, regardless of whether the lens of the eyeglasses the subject 3 wears is a monofocal lens or a progressive power lens with high precision and in addition measure the transmission position data of the lens of the eyeglasses 2 with high precision.

Design of Progressive Power Spectacle Lens

The results of measurements by the thus calibrated line of sight detection device 1 may be used in design of new progressive power spectacle lenses. The flowchart illustrating the procedure of designing the progressive power spectacle lenses is the same as that shown in FIG. 7 relating to the first embodiment. Hereafter, explanation is made referring to FIG. 7 relating to the first embodiment.

In step S11, the subject wearing a reference spectacle lens is put in a specified environment and the line of sight information (gaze position data and transmission position data) of the subject is measured by the line of sight detection device 1. The "reference spectacle lens" is a spectacle lens which is used as a reference for designing a new progressive power spectacle lens. It may be, for instance, a trial model. The calibration of the line of sight detection device 1 by the above method enables measurement of the gaze position data and the transmission position data with high precision.

In step S12, the line of sight information measured in step S11 is evaluated. For instance, the distribution of transmission points is analyzed for the subject who is operating a PC and his gaze point is at the monitor. Using the analyzed distribution of the transmission points, various evaluations are made. For instance, evaluation is made as to which region on the spectacle lens is used when the subject gazes at the monitor, how far the monitor is from the eyeball, what a relationship is between the distance of the monitor from the eyeball and addition, what a relationship is between the size of the characters displayed on the monitor the subject gazes at and the amount of astigmatism at the transmission point. Similarly, evaluation is made on the line of sight information when the subject gazes at the keyboard or a document used during the operation of the PC.

In step S13, design of a new progressive power spectacle lens is performed based on the result of evaluation obtained in step S12. Assume that a problem is to design, for instance, a progressive power spectacle lens that is more suited for the operation of a PC. In this case, further assume that the result of the evaluation in step S12 indicates that the subject uses only a region of the spectacle lens that has an amount of astigmatism of 0.5D or less when he gazes at the characters displayed on the monitor while he uses also a region of the spectacle lens that has an amount of astigmatism of up to 1.5D when he gazes at the keyboard. Then, a target for design may be decided as follows. For the region of addition that corresponds to the distance of the eyeball to the monitor, the amount of astigmatism is set at a reduced level of 0.5D or less and for the region of addition that corresponds to the distance of the eyeball to the keyboard, the amount of astigmatism of up to 1.5D is allowed. Thus a new progressive power spectacle lens can be designed according to this target.

As explained above, the transmission position data measured by the line of sight detection device 1 calibrated by the calibration method using the corner cube 40 may be analyzed and lenses of eyeglasses may be designed based on the result of this analysis. This enables design of lenses of eyeglasses based on the transmission position data with high precision.

The above is exemplary and the present invention is not limited to the above-mentioned design method. For instance, a target for more versatile design may be established by increasing the number of subjects or increasing the number of types of measurement environments.

Manufacture and Sales of Progressive Power Spectacle Lens

Next, the procedure of manufacturing the new progressive power spectacle lens designed by using the result of measurement by the line of sight detection device 1 and distributing the product is explained referring to the flowchart illustrated in FIG. 8. This procedure is the same as that shown in FIG. 8 relating to the first embodiment. Hereafter, explanation is made referring to the flowchart illustrated in FIG. 8.

In FIG. 8, the procedure of measuring the line of sight information of the subject and evaluating the result in steps S21 to S23 and designing a progressive power spectacle lens using the result of the evaluation is the same as the procedure in steps S11 to S13 in FIG. 9.

Then, in step S24, the new progressive power spectacle lens designed in step S23 is manufactured. In step S25, the line of sight information of the subject wearing the new progressive power spectacle lens manufactured in step S24 is measured again in the same manner as in step S21. The result is evaluated again in step S26. In step S27, it is determined whether the new progressive power spectacle lens is perfect as a product by, for instance, checking predetermined target performance. If the lens is perfect, the control proceeds to step S28. If it is imperfect, the control returns to step S23.

In the step S23 to which the control returned, the previous design in step S23 is modified reflecting the result of evaluation in step S26 to perform redesign. Steps S24 to S26 are repeated again and the result is judged again in step S27. This procedure of steps S23 to S27 is repeated any desired times to increase degree of perfection of the new progressive power spectacle lens. Then, the degree of perfection reaches a predetermined degree, a positive judgment is made in step S27 and the control proceeds to S28. The new progressive power spectacle lens is put on the market as a product.

As explained above, the transmission position data measured by the line of sight detection device 1 calibrated by the calibration using the corner cube 40 may be analyzed and lenses of eyeglasses may be manufactured based on the result of this analysis. This enables manufacture of lenses of eyeglasses based on the transmission position data with high precision.

Selection of Progressive Power Spectacle Lens

Figure 22:
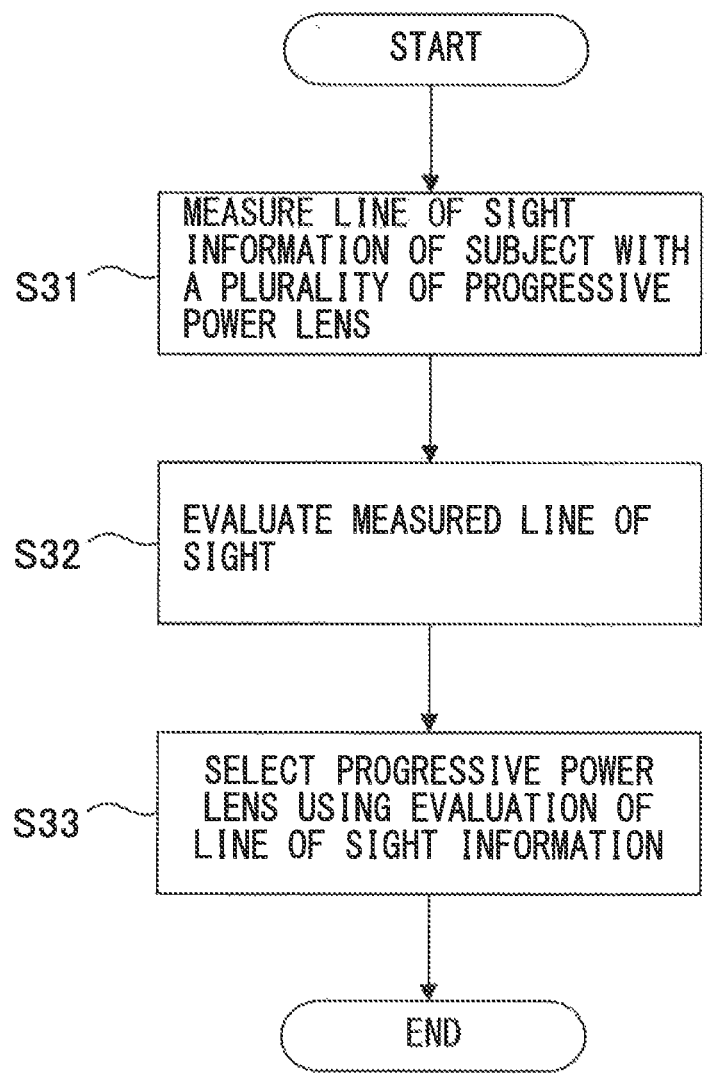
FIG. 22 is a flowchart illustrating a procedure of selecting a spectacle lens.

The results of measurements by the line of sight detection device 1 may be used for selecting a progressive power spectacle lens that fits best to the subject from a plurality of progressive power spectacle lenses having different characteristics from each other. FIG. 22 is a flowchart illustrating the procedure of selecting such a best fit progressive power spectacle lens.

In step S31, a plurality of, e.g., three progressive power spectacle lenses are provided as options. The line of sight detection device 1 measures the line of sight information of the subject for each spectacle lens when he wears it. The three progressive power spectacle lenses differ in characteristics from each other. For instance, one of them is the progressive power spectacle lens the subject now uses and the other two are trial lenses, which are new candidate eyeglasses for purchase. The measurement of the line of sight information is performed in the same manner as that in step S11 of FIG. 9. The environment in which the subject is placed is the same for all the measurements.

In step S32, the line of sight information measured in step S31 is evaluated. For instance, which one of the three progressive power spectacle lenses has the widest distribution of transmission position data is evaluated. The subject can compare the line of sight measurement reports on the results of measurements using the three progressive power spectacle lenses with each other to perform objective evaluations as to whether they fit to him when he wears them.

In step S33, one progressive power spectacle lens is selected from the three progressive power spectacle lenses based on the result of evaluation in step S32. If, for instance, a progressive power spectacle lens that allows use of the widest region of the progressive power spectacle lens is deemed to be good, one having the widest distribution of the transmission position data may be selected from the three progressive power spectacle lenses.

As explained above, the transmission position data measured by the line of sight detection device 1 calibrated by the calibration method using the corner cube 40 may be analyzed and lenses of eyeglasses may be selected based on the result of this analysis. This enables selection of lenses of eyeglasses that is performed based on the transmission position data with high precision.

The third embodiment explained above provides the following operations and advantageous effects.

(1) The method of calibrating the line of sight detection device 1 includes a measurement step of measuring a movement of an eyeball of a subject 3 by a line of sight detection device 1 in a condition in which baselines 31 to 33 are arranged at a predetermined position (i.e., on a reference board 30 attached to an outer peripheral part of a lens of eyeglasses 2) and the baselines 31 to 33 reflected in a corner cube 40 correspond to any three of lines 51 to 56 consisting of ridgelines of the corner cube 40 and images of the ridgelines; and a calibration step of calibrating the line of sight detection device 1 based on the result of measurement by the measurement step. This enables calibration without installing any member in a region of a spectacle lens where the line of sight of the subject passes through. Consequently, as compared with the calibration method using an occluder, the calibration method according to the third embodiment enables calibration of transmission points with high precision. In addition, the calibration method according to the third embodiment saves the trouble of processing a sheet having a special transmission rate characteristic and allows calibration to be performed easily.

(2) In the calibration method (1) above, the measurement step uses the lines 51 to 56 consisting of the ridgelines of the corner cube 40 and lines corresponding to the images of the ridgelines. This enables calibration to be performed easily without further processing of the corner cube 40.

Variation Example 1

In the above-mentioned embodiment, the example is explained, in which upon calibration of the gaze position data, an mark plate 21 as shown in FIG. 15 is used. However, the present invention is not limited to this. For instance, as shown in FIG. 23 A, the mark plate 21 that have marks 22 arranged at a further increased density according to the refractive power of the lens of the eyeglasses 2 may be used.

For instance, as shown in FIG. 23 B, the in mark plate 21 that has the marks 22 arranged at higher density in a region corresponding to the peripheral part of the field of view may be used. When the subject 3 gazes at the peripheral part of the field of view, the precision of detection of the eyeball movement data is lower at the peripheral part than at the central part of the field of view due to blocking of light to the pupil by the eyelid and due to the asphericity of the cornea surface. Therefore, as shown in FIG. 23 B, arranging the marks 22 at high density in a region corresponding to the peripheral part of the field of view makes up for such a decrease in the detection precision.

Figure 23A:
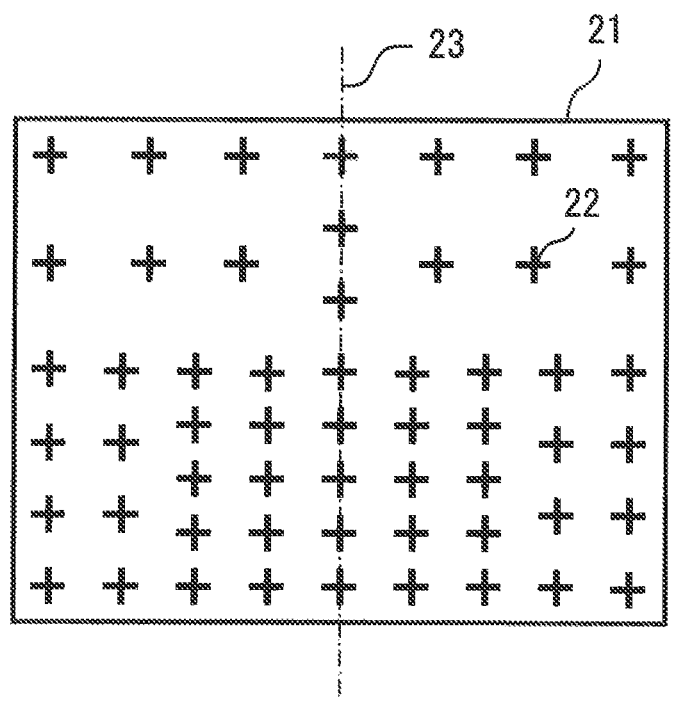
FIG. 23A-23D are diagrams illustrating examples of the layout of marks in Variation Example 1.
Figure 23B:
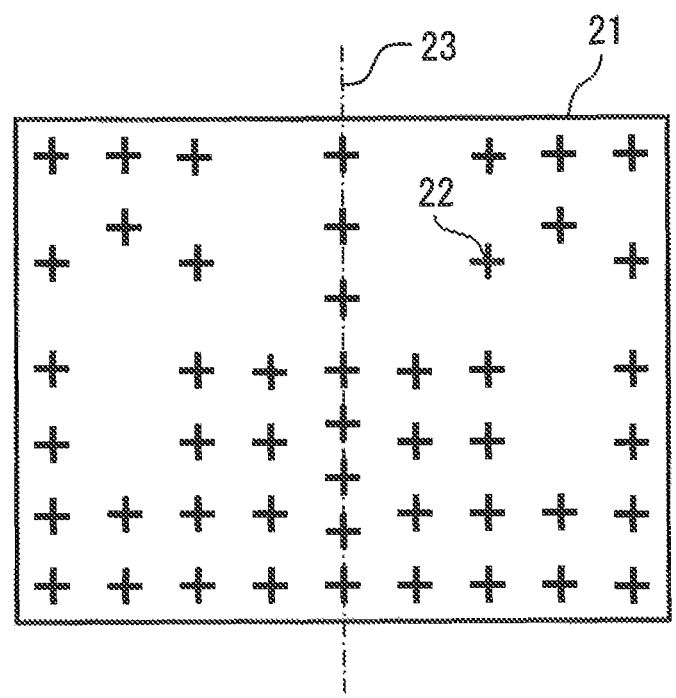
Figure 23C:
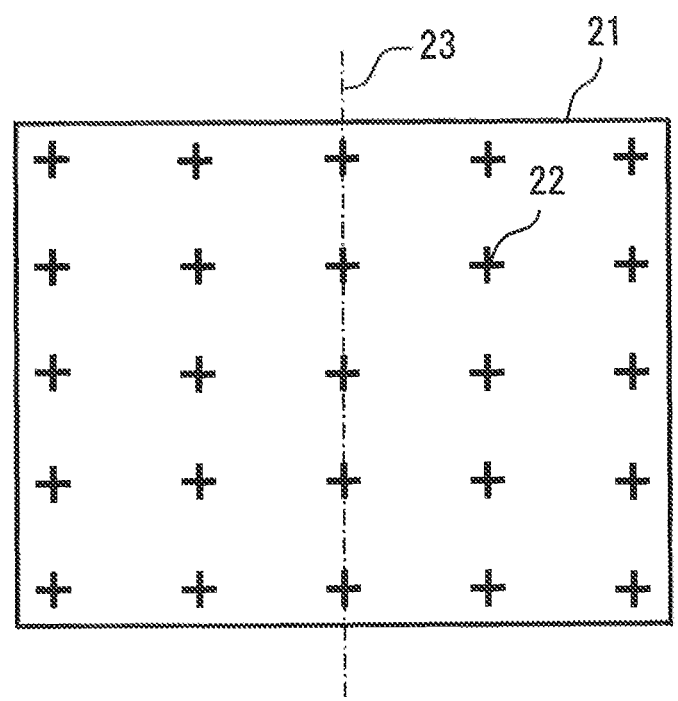
Figure 23D:
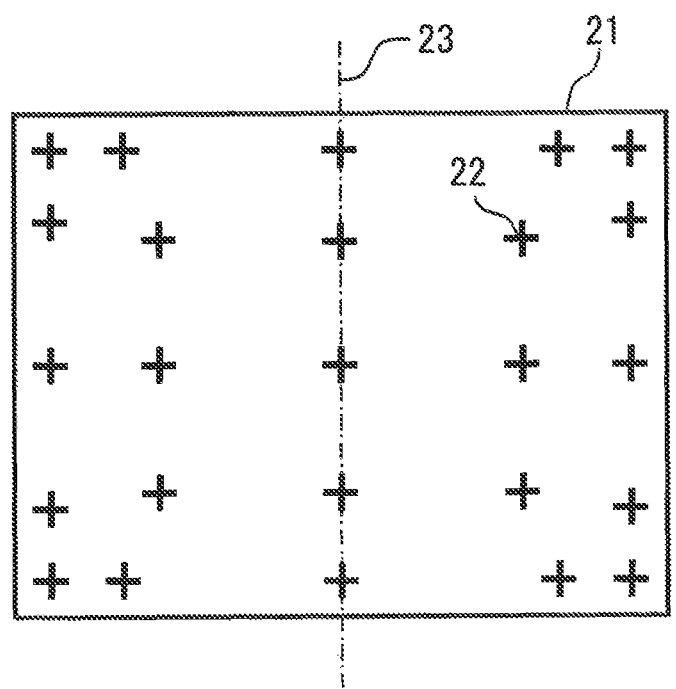

The lens of the eyeglasses 2, which may be of any type, such as a monofocal spherical lens, a monofocal aspheric lens or a progressive power lens, has stronger distortion at the peripheral part of the field of view. This is particularly so for a lens having a greater spherical diopter power. In this case, as shown in FIG. 23 C, the mark plate 21 that has the mark 22 arranged uniformly may be used. Alternatively, to correct strong distortion at the peripheral part of the field of view according to the magnitude of the spherical diopter power with high precision, the mark plate 21 that has the marks 22 arranged at the peripheral part as shown in FIG. 23D may be used.

Variation Example 2

Figure 24:
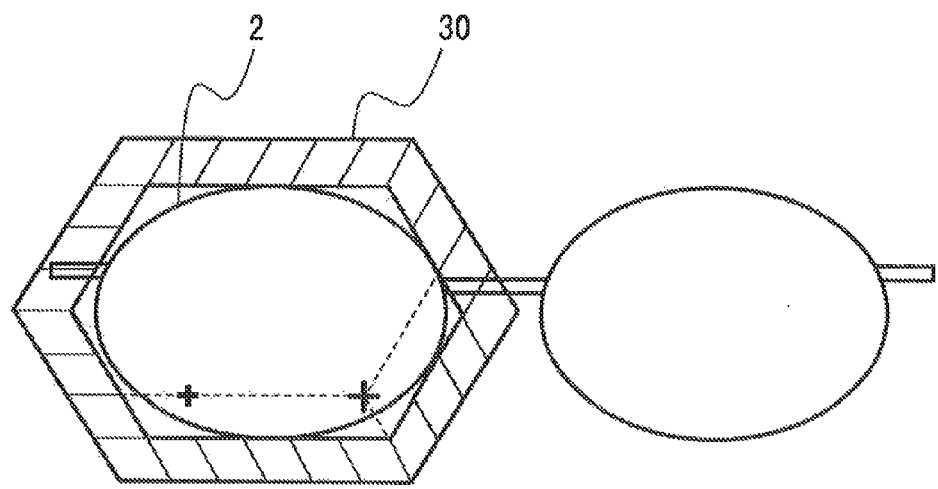
FIG. 24 is a diagram illustrating a reference board in Variation Example 2.

In the above embodiment, the example is explained in which the transmission position data is calibrated using the reference board 30 shown in FIG. 16. However, the present invention is not limited to this. For instance, the reference board 30 as shown in FIG. 24 may be used. The reference board 30 as shown in FIG. 24 is configured to be larger than the reference board 30 shown in FIG. 16 so that almost the whole lens of the eyeglasses 2 can be inside the reference board 30 of the ring shape. This enables the measurement with a wider field of view.

Variation Example 3

In the above embodiment, explanation is made on the basis that the ring-shaped reference board 30 is planar and has the axes of coordinates on the same plane as that of the reference board 30. However, the present invention is not limited to this. For instance, the transmission position data measured using the reference board 30 as a reference may be converted into data of the coordinates system to be used in designing the lens of the eyeglasses 2. For any eyeglasses 2 having a relatively large curvature, the reference board 30 may have a contour other than planar. For instance, it may be curved along the curve of the lens.

Variation Example 4

In the above embodiment, the example is explained in which the reference board 30 has baselines 31 to 33 depicted in three different directions. However, the present invention is not limited to this. For instance, the reference board having baselines 30 depicted in at least two different directions to enable determination of the positions of the transmission points on the lens of the eyeglasses 2 may be used. In this case, the line of sight detection device 1 measures the eyeball movement data in a condition in which the baselines in the two directions correspond to any three of the lines 51 to 56 consisting of the ridgelines of the corner cube 40 and lines of the images of the ridgelines of the corner cube 40.

Variation Example 5

In the above embodiment, the example is explained in which upon measurement of the transmission position data to calibrate the eyeball movement data, the baselines 31 to 33 on the reference board correspond to any three of the lines 51 to 56 consisting of the ridgelines of the corner cube 40 and lines that correspond to images of the ridgelines of the corner cube 40. However, the present invention is not limited to this. For instance, the baselines 31 to 33 on the reference board 30 may correspond to baselines preliminarily depicted on the corner cube 40 instead of the ridgelines of the corner cube 40.

Variation Example 6

In the above embodiment, the example is explained in which the reference board 30 having depicted baselines 31 to 33 is attached to the eyeglasses 2. However, the baselines 31 to 33 may be arranged at the outer peripheral part of the lens of the eyeglasses by a method other than this method. For instance, for measurements made for the subject 3 wearing a frame for ocular examination (optometry) capable of removably holding a test lens, the baselines 31 to 33 may be depicted on a lens holder part (i.e., an outer peripheral part) of the frame for ocular examination.

Variation Example 7

In the above embodiment, the example is explained in which the transmission position data is calculated from the eyeball movement data. However, for a case in which the relationship between the eyeball movement data and the gaze position data is calibrated with sufficient precision similarly to the above-mentioned embodiment, the transmission position data may be calculated from the gaze position data. In this case, the relationship between the gaze position data and the transmission position data may be calibrated.

To calculate the transmission position data from the gaze position data, a conversion formula, for instance, a fourth order polynomial formula including the gaze position data (X, Y) as two variables is used similarly to the formulas (3) and (4) above. By determining the coefficients of the conversion formula, the relationship between the gaze position data and the transmission position data is calibrated. Concretely, as shown in FIG. 17, the subject 3 moves, for instance, his hand or neck to adjust the positional relationship between the corner cube 40 and his head and changes the position at which the line of sight 42. Then, as shown in FIG. 18, he adjusts such positional relationship so that any three of the lines 51 to 56, which consist of the ridgelines of the corner cube 40 and lines corresponding to images of the ridgelines, can be superimposed on the predetermined baselines 31*c* to 33*c* on the reference board 30. The line of sight detection device 1 records the image captured by the forward field of view camera 10 when the subject 3 gazes the top 41 of the corner cube 40. The calibration computation device 18 detects the position of the top 41 of the corner cube 40 in the captured image as gaze position data. The lens center of the forward field of view camera 10 corresponds to the top 41 of the corner cube 40 reflected in the captured image and thus the position of the top 41 of the corner cube 40 can be determined from the captured image. The calibration computation device 18 determines the coefficients of the conversion formula by the least square method so that the position of the transmission point calculated from the detected gaze position data according to the conversion formula corresponds to the intersection point of the lines extending from the baselines 31*c* to 33*c*.

The relationship between the gaze position data and the transmission position data may be calibrated by measuring the movement of the eyeball of the subject 3 in the condition shown in FIG. 18 using the line of sight detection device 1 and determining the gaze position data from the result of the measurement according to the equations (1) and (2) above. In this case, the coefficients of the conversion formula are determined by the least square method so that the transmission point calculated from the gaze position data according to the conversion formula corresponds to the intersection point of the lines extending from the baselines 31*c* to 33*c*.

Variation Example 7, like the embodiment mentioned above, enables calibration without installing any member in a region where the line of sight of the subject 3 passes through the spectacle lens. Consequently, Variation Example 7 enables calibration of the transmission point with higher precision than the calibration method using an occluder.

Variation Example 8

In the above embodiment, the example is explained in which the gaze position data and the transmission position data are calculated using differences in coordinates between the center of pupil and center of cornea reflection, say, value (x, y) in the equations (1) to (4). However, the gaze position data and the transmission position data may be calculated by using only the coordinates of the center of pupil. This is suited for the case in which the field of view to be measured is too wide to measure the coordinates of the center of cornea reflection.

Variation Example 9

In the above embodiment, the example is explained in which the calibration computation of the gaze position data and the transmission position data is carried out by the calibration computation device 18. However, the calibration computation may be carried out by arithmetic processing on a PC using software. In particular, the calibration may be divided into a plurality of stages using the conventional device, with a preceding stage being carried out by processing with hardware and a subsequent stage being carried out by processing on the PC using software. This processing may be carried out real-time while the subject 3 gazes at a target object or may be subjected to post-processing using the stored image if the processing speed is limited.

Variation Example 10

In the above embodiment, the example is explained in which the present invention is adopted by the line of sight detection device 1 of the type that is attached to the head of the subject 3 as shown in FIG. 1. However, the present invention is not limited to this. It is sufficient that the device 1 has a function of measuring relative movement of the eyeball relative to the head of the subject 3. For instance, the present invention may be adopted by an assembly of a stationary line of sight detection device and a different device that detects the movement of the head of the subject 3.

Fourth Embodiment

Figure 25:
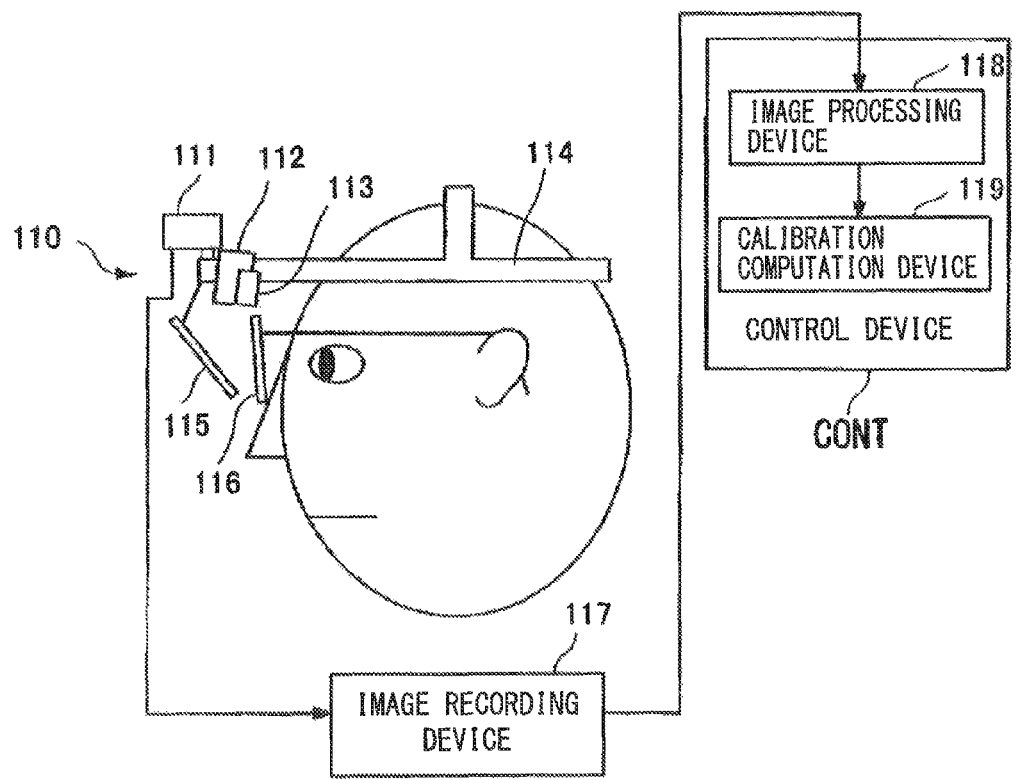
FIG. 25 is a schematic diagram illustrating the construction of a line of sight detection device according to a fourth embodiment of the present invention.

A fourth embodiment according to the present invention is explained. The explanation of the fourth embodiment contains some parts that overlap with the explanation of the third embodiment. For the sake of convenience, the overlapping parts are also explained here. FIG. 25 is a schematic diagram showing the construction of a line of sight detection device (optical device) 110 according to this embodiment. As shown in FIG. 25, the line of sight detection device 110 is attached to the head of the subject wearing, for instance, progressive power eyeglasses (optical instrument) 116 in use.

The line of sight detection device 110 includes a forward field of view 111, an eyeball imaging camera 112, an infrared LED 113, a headband 114, a dichroic mirror 115, an image recording device 117, an image processing device 118, a calibration computation device 119, and a control device CONT. The subject can see the forward range of vision freely via the progressive power eyeglasses 116 and the dichroic mirror 115 that transmits visible light.

The control device CONT may be, for instance, an information processing device such as a personal computer. The image recording device 117 is portable that for instance a subject can carry. The image processing device 118 and the calibration computation device 119 are loaded in, for example, a slot of the control device CONT as boards.

The forward field of view camera 111 is fixed to face substantially in the same direction as the field of view in front of the subject or slightly downward to that direction.

The forward field of view camera 111 captures a moving image of horizontal angle of view of about 90 degrees in front of the subject. The image captured by the forward field of view Ill is recorded at the image recording device 117.

The infrared LED 113 is a light source for irradiating infrared light. The infrared light irradiated from the infrared LED is reflected by the dichroic mirror 115 to illuminate the eyeball of the subject. The eyeball imaging camera 112 captures a moving image of the eyeball illuminated with the infrared light, the eyeball imaging camera 112 are installed In total two eyeball imaging camera 112 are installed, one for right eye and the other for the left eye. The eyeball imaging camera 112 is focused on each of the left and right eyes via the dichroic mirror 115. The images of the left and right eyes captured by the eyeball imaging camera 112 are recorded individually by the image recording device 117.

The images recorded by the image recording device 117, that is, the image captured by the forward field of view camera 111 and the image of eyeball captured by the eyeball imaging camera 112 are transmitted to, for example, the image processing device 118.

The image processing device 118 determines, for example, the coordinates of the center of pupil and the coordinates of the center of cornea reflection in the image of the image of eyeball transmitted from the image recording device 117 and outputs them as eyeball movement information in chronological order. The image processing device 118 transmits the outputted eyeball movement information to, for instance, the calibration computation device 119.

The calibration computation device 119 performs arithmetic processing of the eyeball movement information outputted from the image processing device 118 to calculate line of sight information such as gaze point and transmission point and outputs the result of calculation in chronological order. The arithmetic processing is performed in a first calibration computation step by a first calibration computation unit and a second calibration computation step by a second calibration computation unit. The first calibration computation unit calculates the line of sight information based on the movement information of the eyeball. The second calibration computation unit corrects the errors of the line of sight information caused by the refractive action at the lens 116 of the eyeglasses exerted on the line of sight and the image of eyeball captured by the eyeball imaging camera 112. The first and second calibration computation units may be integrated to each other. An integrated calibration computation unit calculates, in a calibration computation step, the line of sight information of which the error caused by the refractive action at the lens of the eyeglasses 116 is corrected based on the movement information about the eyeball.

The gaze position data is data that includes coordinates of the gaze point in the image of the forward field of view captured by the forward field of view camera 111.

The transmission position data is data that includes the coordinates of the transmission position on the spectacle lens. That is, the transmission position data is coordinates data on a surface that is the progressive power surface of the spectacle lens 116. The transmission position data includes coordinates data of a surface of the spectacle lens 116 on the side of the eyeball and coordinates data of a surface of the spectacle lens 116 on the side opposite to the eyeball either one of them or both of them may be used. The calibration computation device 119 uses the calibrated data described later upon the computation processing.

The control device CONT has a memory unit, which is not shown in the drawings. The control device CONT is capable of recording the images recorded by the image recording device 117, the movement information of the eyeball outputted at the image processing device 118, the gaze position data and the transmission position data outputted at the calibration computation device 119 at the memory unit.

The control device CONT is connected to, for instance a monitor or an external memory device, which are not shown in the drawings. In this case, the control device CONT is capable of outputting to, for instance, a monitor and recording in a recording medium, for instance, an external memory device, the images recorded by the image recording device 117, the movement information of the eyeball outputted at the image processing device 118, the gaze position data and the transmission position data outputted at the calibration computation device 119.

The control device CONT is capable of outputting the gaze position data from the calibration computation device 119 in a condition in which a mark, for instance, a point or a circle is superimposed on the image of the forward field of view transmitted from the image recording device 117. The position at which the mark is superimposed corresponds to the coordinates on the image of the forward field of view indicated by the gaze position data. The control device CONT is capable of displaying a cumulative frequency map of the gaze position data based on the gaze position or record such a map at the recording unit or external memory medium.

The control device CONT is capable of displaying coordinates of the transmission position data outputted at the calibration computation device 119 or recording them at the memory unit or the external memory device. In this case, similarly to the case in which the gaze position data is outputted, the image of the spectacle lens 116 or drawing are displayed on the monitor, on which an image may be displayed in which a mark is superimposed on the coordinates that corresponds to the transmission position data or a cumulative frequency map.

As explained above, the image of eyeball captured by the eyeball imaging camera 112 is once recorded at the image recording device 117 and then reproduced and transmitted to the image processing device 118. However, the captured image may be recorded at the image recording device 117 and at the same time transmitted to the image processing device 118. This enables determination of the gaze position data and the transmission position data simultaneously with the measurement of the line of sight.

Next, the calibration method at the calibration computation device 119 is explained. Here, explanation is made assuming that the first and second calibration computation steps are combined with each other.

The coordinates of the centers of pupil and of the cornea reflection, which constitute the movement information of the eyeball, are converted into the coordinates of the gaze point, which constitute the gaze position data, and the coordinates of the transmission position on the spectacle lens according to equations each with a plurality of coefficients, respectively. The conversion formulas may individually express horizontal coordinates or vertical coordinates of the gaze position and transmission position each by a single formula, or by a plurality of formulas separated into several regions depending on the gaze position and the transition position. In the latter case, preferably the formulas are connected smoothly with each other. These conversion formulas are designed to have sufficient degree of freedom to express complexity of conversion due to the characteristic distribution of the refractive power of the progressive power spectacle lens.

In the measurements for calibration, the range of measurement of the line of sight is important. If the range of measurement is too narrow as compared with the field of view, no data useful for calibration can be obtained at the peripheral part of the field of view. Consequently, the precision of calibration at the peripheral part of the field of view decreases. On the contrary, if the range of measurement is too wide as compared with the field of view, data at a position out of the field of view, which is thus useless for and unavailable to calibration, increases and accordingly effective data useful for the calibration decreases. Therefore, not only the efficiency of calibration operation decreases but also the precision of calibration decreases and the number of data necessary for calibration becomes difficult to obtain. This leads to failure of calibration.

Therefore, for a reference for a minimum required range, the size of the spectacle lens for ocular examination used at eyeglasses shops for purchasers is adopted as a reference. The effective size of a circular lens for ocular examination is about 35 mm. Assume that the distance of the point of rotation of the eyeball to the lens for ocular examination is 25 mm, which is converted into an angle range of the line of sight of about ±35 degrees. Further, if the size of the pupil is 6 mm in diameter, an angle range allowing all the light fluxes that enter the pupil is about ±30 degrees. That is, it is preferred to set a range of about 60 degrees in total to be a range of measurement for calibration.

However, the diameter of 35 mm is too narrow for the progressive power spectacle lens to allow it to test its characteristic sufficiently. Thus, for a trial lens, which is used in combination with a lens for ocular examination, a lens only a lower part of which is elongated is used. Most of frames for commonly used eyeglasses are larger as compared with the lens for ocular examination in portions ranging from the center to downward or in the horizontal direction. In particular, most of them have a width of exceeding 50 mm. Therefore, the spectacle lens is originally designed and manufactured to have a diameter of 50 mm or more.

From this, a maximum required range is about 50 mm in diameter, or about 50 mm wide in lateral direction and about 25 mm long downward and about 15 mm long upward in the vertical direction. This range is converted in terms of angle to about 90 degrees in full width or ± about 45 degrees in the horizontal direction, about 45 degrees downward and about 30 degrees upward.

Both the relationship between the movement information of the eyeball and the gaze position data and the relationship between the movement information of the eyeball and the transmission position data are nonlinear. Thus, to convert the data, at least second order polynomial formulas are necessary for each of two variables, one in the vertical direction (Y direction) and the other in the horizontal direction (X direction). In this case, the movement information of the eyeball, the gaze position data, and the transmission position data are measured when the subject gazes at three sets or more in each of X and Y directions in total 9 or more marks for calibration and the coefficients of two-variant second order polynomial formula can be determined from the measured data by the least square method.

To increase the precision of conversion, a higher order formula is required. For instance, for any lens of eyeglasses 116 which is a simple monofocal spherical lens, the relationship between the position of the transmission point of the line of sight at the lens of the eyeglasses 116 and a shift of the terminal point of the line of sight due to the refraction is a nonlinear relationship to be expressed by a third order or higher formula. This relates to the third-order aberration that the lateral spherical aberration of a spherical lens is proportional to a cube of the height of light that passes the entrance pupil from the light axis. This means that the relationship between the transmission position data and strictly the gaze position data is inconvertible by a second-order polynomial formula. For any range of measurement of the line of sight wider than, for instance, ± about 30 degrees or further ± about 45 degrees, the relationship of interest is higher than a third-order. For a progressive power lens, the relationship of interest is rotationally asymmetric and thus is more complicated.

In addition, the relationship between the transmission position data and the gaze position data is influenced by, for instance, asphericity of the shape of the cornea surface and distortion aberration between the forward field of view camera 111 and the eyeball imaging camera 112. Thus, it is necessary to increase the order of the polynomial formula used for conversion as the field of view for the measurement of the line of sight is wider. Consequently, it is preferred to use a third- or fourth-order polynomial formula instead of a second-order one.

Thus, the conversion formula can be expressed by using two-variant fourth-order polynomial formula, such as, for instance, [Math. 1], [Math. 2], [Math. 3], and [Math. 4] below. That is, to express the deviation of the line of sight due to the diffraction by the eyeglasses with sufficient precision, third-order higher formula is necessary for a field of view narrower than ±30 degrees and at least a fourth-order formula is necessary for a field view of wider than ±30 degrees.

$$X = A_{44}x^4y^4 + A_{43}x^4y^3 + A_{34}x^3y^4 + \ldots + A_{11}xy + A_{01}y + A_{10}x + A_{00}$$ [Math 1]

$$Y = B_{44}x^4y^4 + B_{43}x^4y^3 + B_{34}x^3y^4 + \ldots + B_{11}xy + B_{01}y + B_{10}x + B_{00}$$ [Math 2]

$$X' = A'_{44}x^4y^4 + A'_{43}x^4y^3 + A'_{34}x^3y^4 + \ldots + A'_{11}xy + A'_{01}y + A'_{10}x + A'_{00}$$ [Math 3]

$$Y' = B'_{44}x^4y^4 + B'_{43}x^4y^3 + B'_{34}x^3y^4 + \ldots + B'_{11}xy + B'_{01}y + B'_{10}x + B'_{00}$$ [Math 4]

In the above formulas, [Math. 1] and [Math. 2] represent conversion formulas for converting the eyeball movement information and the gaze position data, respectively. X and Y are coordinates of the gaze point. On the other hand, x and y are values of differences between the coordinates of pupil and of center of cornea reflection. [Math. 3] and [Math. 4] represent conversion formulas for the eyeball movement information and the transmission position data of the line of sight at the lens of the eyeglasses 116. X' and Y' are coordinates of the transmission position at the lens of the eyeglasses 116. On the other hand, x and y are values of differences between the coordinates of pupil and of center of cornea reflection. The coefficients in the conversion formulas are actually measured for each subject and preferably for each measurement and calibrated.

The calibration of the coefficients of the conversion formulas enables correction of aberrations, for instance, deviations caused by the condition of the attachment of the line of sight detection device 110 to the head of the subject or the interindividual difference of the shape of the eyeball of the subject, the deviation of the line of sight caused by diffraction at the lens of the eyeglasses 116, and distortion of the image of eyeball caused by diffraction at the lens of the eyeglasses 116, and distortion of the field of view caused by the aberration of the forward field of view camera, and aberrations caused by differences of the left and right eye and the position of the forward field of view camera.

The calibration of the movement information of the eyeball and the gaze position data is achieved by determining the coefficients of the formulas of [Math. 1] and [Math. 2] by the calibration computation device according to the least square method when the subject gazes at a plurality of stationary marks, the position of which with respect to the subject is known, so that the gaze position data calculated from the movement information of the eyeball corresponds to the position of the marks.

Figure 26:
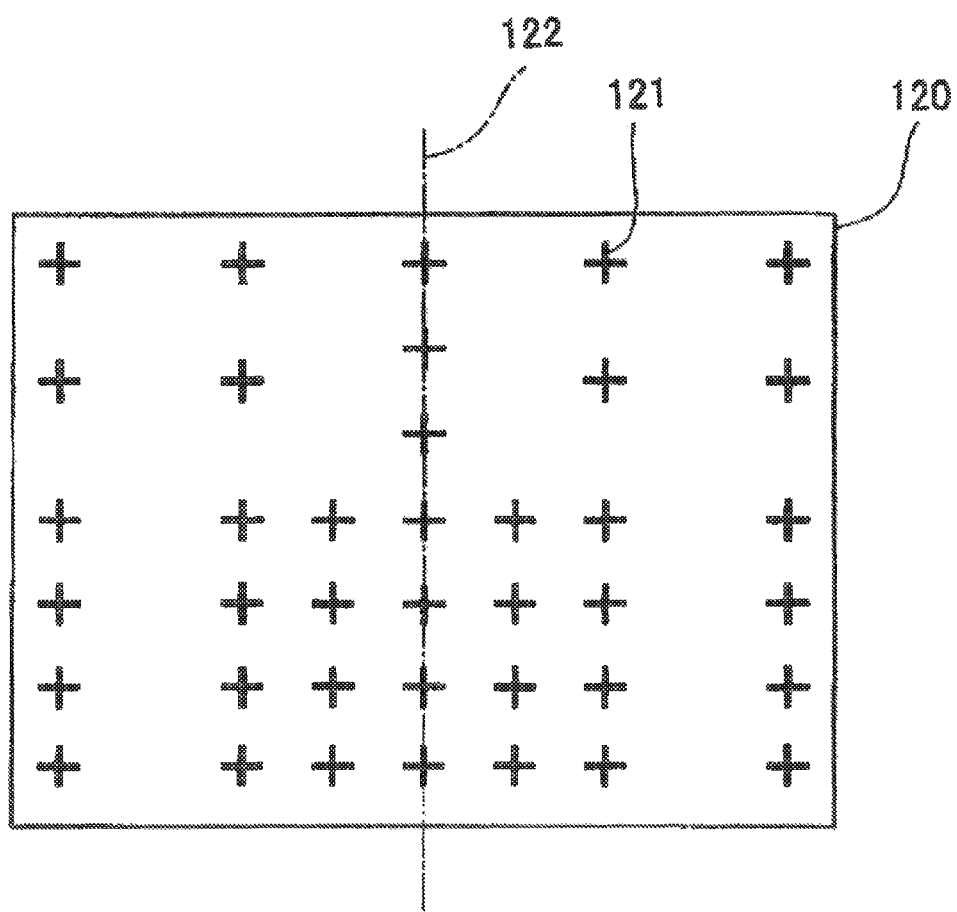
FIG. 26 is a diagram illustrating the layout of marks for calibration according to the fourth embodiment.

FIG. 26 is a diagram illustrating the arrangement of marks for calibration. As shown in FIG. 26, the marks 121 are printed on the mark plate 120. The mark plate 120 is placed at a distance of, for instance 2 m from the subject and is arranged in the central direction of the field of view of the subject and in addition all of them are arranged within the field of view of the forward field of view camera. The marks 121 are arranged within the range where the angle of view at least in the horizontal direction exceeds 60 degrees, which range preferably covers substantially all the range of field of view that the subject can see with the eyeglasses. They are arranged at higher density as the refractive power of the progressive power spectacle lens through which the subject gazes at them is more characteristic.

The marks 121 are arranged at least 5 points in each of the vertical direction (Y direction) and the horizontal direction (X direction) in total at least 25 points. This enables determination of all the coefficients of the fourth-order formulas in the equations (1) and (2) by the least square method.

Concretely, the marks are arranged within the range of ±45 degrees in the horizontal direction, 30 degrees upward and 45 degrees downward in the vertical direction. The marks are arranged in high densities on a vertical line 122 that passes through the center of the field of view of the subject and in a region lower than the center of the field of view of the subject. These ranges correspond to the area on the principal line and the progressive power zone between the region for distance vision and the region for reading, respectively, on the progressive power spectacle lens.

The region in which marks are arranged in higher density provides higher precision of the calibration data determined by the least square method and also allows for verification of the precision. This is convenient for efficiently perform calibration computation with high precision when eyeglasses is used, which has a characteristic distribution of refractive power, such as a progressive power spectacle lens.

For any progressive power lens, the range on the principal line at the progressive power part and by about 20 mm downward from the center is a region in which the change in distribution is characteristic. In this range, the addition changes by at most about 4 diopters. Thus, four or more marks arranged at this part provide an arrangement of marks with a density higher that pitch of less than 1 diopter. This enables calibration and verification of the progressive power part with sufficient precision.

This configuration enables the precision of calibration of the line of sight, in particular at the progressive power part to be an angle of 2 degrees or less. The angle of 2 degrees of the line of sight is converted into the coordinates of the transmission point of the spectacle lens of about 1 mm. The precision of 1 mm is sufficient since the specifications such as progressive zone length and inset amount are designed on the order of mm.

The gaze point data calibration may be measured using any one of marks on the mark plate 120 and thus more marks 121 are used to measure necessary data at a portion the precision of which is desired to be more increased. All the marks 121 are labeled. The label actually used for the measurement is notified to the calibration computation device via the control device CONT and the calibration computation device 119 calculate the calibration data using only the data of the mark that is used for the measurement. This enables the number of the calibration data to be freely changed and thus adjusted, if necessary, with confirming the precision of the calibration.

To calibrate the aberration due to a difference in position between the left and right eyes and the forward field of view camera, the distance between the mark plate 120 and the subject needs to be set at a plurality of known distances, for instance, 1 m or 0.2 m in addition to 2 m, and measurement needs to be made at each distance. In this case, the mark of only one point in the center of the field of view is used for the measurement.

The calibration of the movement information of the eyeball and the transmission position data is achieved by determining the coefficients of the formulas of [Math. 3] and [Math. 4] by the calibration computation device 119 according to the least square method when the subject gazes in a direction in which the line of sight passes through a point the position of which on the lens of the eyeglasses 116 known, so that the transmission position data calculated from the movement information of the eyeball corresponds to the position of the transmission point on the lens of the eyeglasses 116. In this case, the number of the gaze point data to be measured for calibration need not be the same as the number of the movement information of the eyeball and the gaze position data and the number of calibration data may be adjusted as necessary with confirming the precision of calibration.

Figure 27:
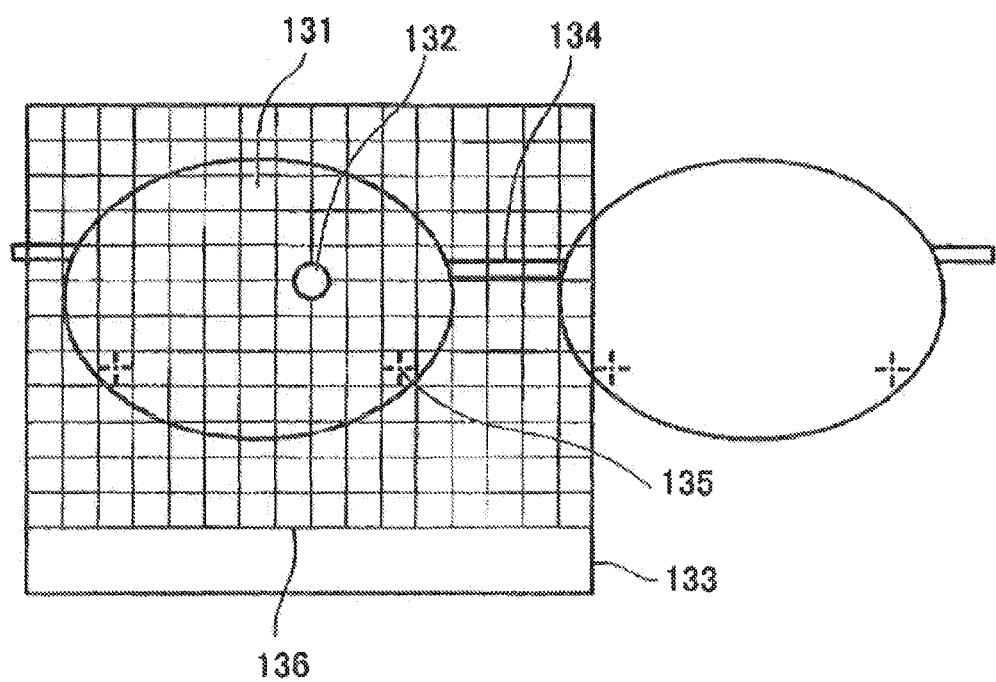
FIG. 27 is a diagram illustrating an example of the method of measuring calibration data according to the fourth embodiment.

FIG. 27 is a diagram illustrating the method of measuring the calibration data on the lens of a progressive power lens of eyeglasses. As shown in FIG. 27, the actual transmission position on the lens 131 of the progressive power spectacle lens is measured as follows. While the subject gazes an mark, a translucent light shielding plate 133 having a hole 132 with a diameter of 1 to 2 mm and a grid pattern 136 is lightly contacted on a surface of the lens 131. The subject gazes at the mark through the center of the hole. In this condition, the position of the center of the hole 132 is defined to be the transition position and that position is subjected to length measurement using the grid pattern on the light shielding plate 133 as a gauge based on the mark 135 the position of which on the eyeglasses frame 134 or the lens 131 is known as a reference. The length measurement may be performed layer based on the recorded image of the eyeball imaging camera.

This enables high precision measurement of the gaze position data of the subject wearing progressive power eyeglasses and also enables high precision measurement of the transmission position data of the spectacle lens.

Figure 28:
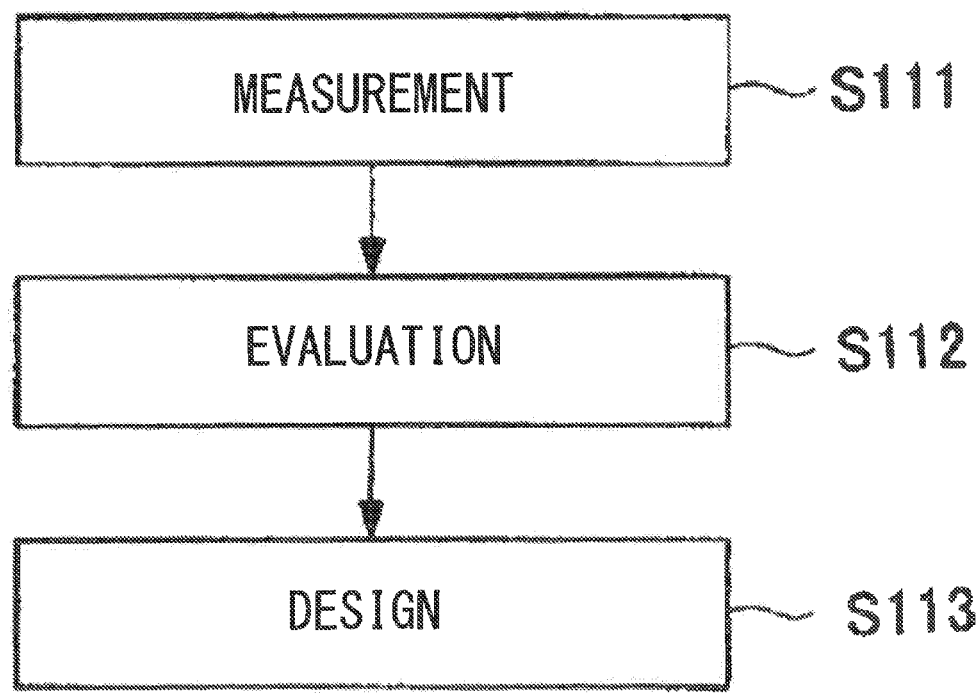
FIG. 28 is a flowchart illustrating a procedure of designing a progressive power spectacle lenses according to the fourth embodiment.

FIG. 28 is a diagram illustrating the procedure of design of a new progressive power spectacle lens. At measurement S111, a subject wearing a reference spectacle lens is placed in a specified environment and the line of sight information in this condition is measured. The reference spectacle lens is a spectacle lens used as a reference upon design of a new progressive power spectacle lens, for instance, a trial model. The specified environment is one of environments in which the new progressive power spectacle lens is supposed to be used, for instance, driving a car.

Accurate line of sight information is measured by using a line of sight tracking device, which calculates line of sight information from the movement information of the eyeball of subject and corrects an error of line of sight information due to the progressive power spectacle lens.

At evaluation S112, the measured line of sight information is evaluated. For instance, analysis of the distribution of the transmission points when the subject gazes at the side view mirror while he is driving a car enables examination, for instance, as to which region on the spectacle lens is used at that moment or to what extent the eyeball and the neck are moved to change the line of sight.

At design S113, a new progressive power lens is designed based on the result of the evaluation. In this case, the design may be performed with setting a design target, for instance, achieving the aberration performance of the progressive power spectacle lens that enables the amount of movement of the neck when the subject gazes the side view mirror to be reduced to 50% of the amount of movement when he wears the reference spectacle lens.

Of course, these are exemplary. For instance, a target for more versatile design may be established by increasing the number of subjects or increasing the number of types of measurement environments.

Figure 29:
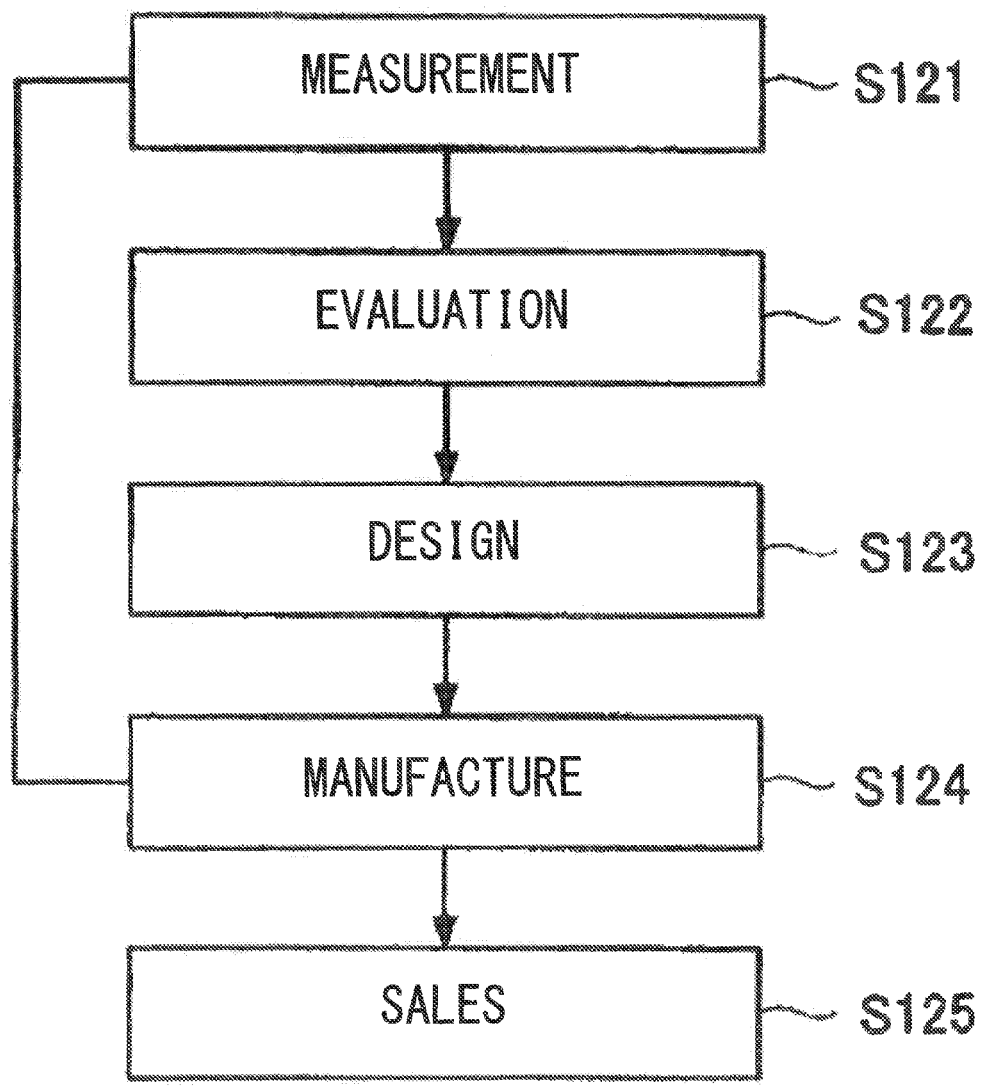
FIG. 29 is a flowchart illustrating a procedure of manufacture and sales of progressive power spectacle lenses according to the fourth embodiment.

FIG. 29 is a diagram illustrating the procedure of manufacturing a new progressive power spectacle lens and selling it as a product.

The procedure is the same as that in FIG. 28 up to the measurement S121, the evaluation S122, and the design S123. However, at the manufacture S124, the new progressive power spectacle lens designed at the design S123 is manufactured as a trial model, which is re-measured at the measurement S121, reevaluated at the evaluation S122, and redesigned at the design S123 for further improvement. This procedure is repeated in any desired times to increase the degree of perfection of the product to be ready for being put on the market.

Figure 30:
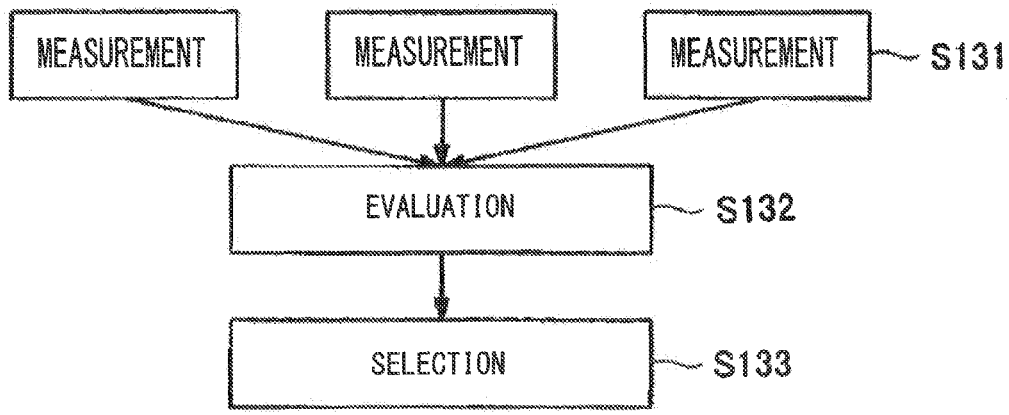
FIG. 30 is a flowchart illustrating a procedure of selecting progressive power spectacle lenses according to the fourth embodiment.

FIG. 30 is a diagram illustrating the procedure of selecting a progressive power spectacle lens that is best fitting to the subject.

At the measurement S131, three progressive power spectacle lenses having different characteristics from each other are picked up. The subject wears each of them for measuring the line of sight information. Each measurement is performed in the same manner as in the measurement S111 illustrated in FIG. 28. The environment in which the subject is placed for each measurement is the same for all the measurements.

At the evaluation S132, the line of sight information measured at the measurement S131 is evaluated for comparison. For instance, which progressive power spectacle lens is has widest distribution of transmission position data is evaluated.

At the S133, a progressive power spectacle lens is selected based on the result of the evaluation S132. For instance, assuming that a spectacle lens allowing use of the widest region of the spectacle lens is best fitting, the spectacle lens manifesting the widest distribution of the transmission position data is selected.

As described above, the data obtained by using the line of sight tracking device according to the present invention can be utilized in, for instance, development of new progressive power lenses and selection of a progressive power lens best fitting to the subject.

Next, explanation is made an example in which the first and second calibration computation steps are performed separately.

In case the calibration is performed in a plurality of steps, first, in a first calibration computation step, error components caused by the condition of attachment of the line of sight detection device to the head of the subject or interindividual difference in the shape of the eyeball of the subject are determined as principal calibration targets by a simpler measurement method.

Figure 31:
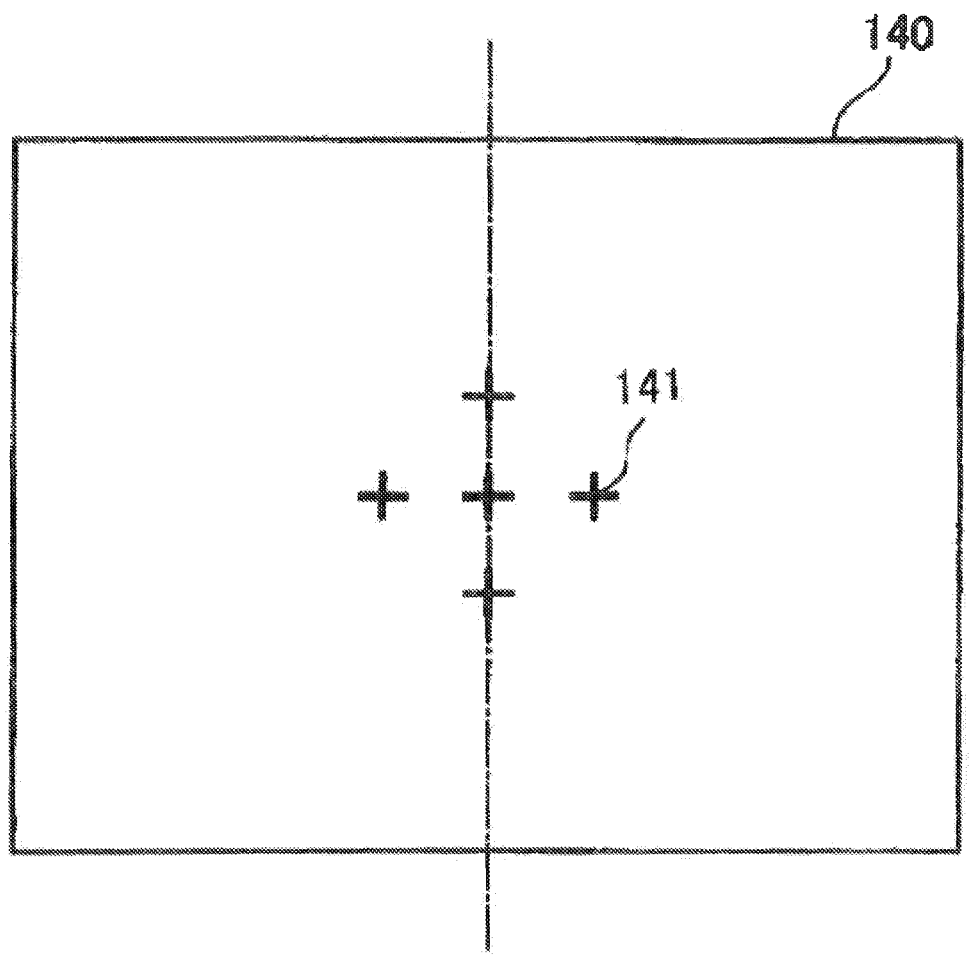
FIG. 31 is a diagram illustrating an example of the layout of marks for calibration in the fourth embodiment.

FIG. 31 is a diagram illustrating the arrangement of the marks for the calibration.

As shown in FIG. 31, only five marks 141 are put on a mark plate 140, one being in the direction of the center of the whole field of view of the subject at a distance of, for instance, 2 m from the subject and four being at upside, downside, left side and right side of the central one. All the five marks are arranged only near the center of the field of view of the subject. In this condition, use of fourth order formulas such as [Math. 1] to [Math. 4] as the conversion formulas for the movement information of the eyeball and the line of sight information without any modification disables determination of any undetermined coefficients by the least square method. Thus, formulas with reduced number of undetermined coefficients, which is modified by, for instance, by order reduction or introduction of the relationship between the coefficients, are used.

In this step, to calibrate the aberration due to a difference between the position of the left and right eyes and the position of the forward field of view camera, the distances between the subject and the marks are varied to allow the subject to gaze at only the central point. In this condition, three distances between the subject and the mark of concern are set, for instance, 1 m, 0.2 m and 2 m. Use of the calibration data in this step alone enables the calibration computation device 119 to perform arithmetic processing of the movement information of the eyeball and output the gaze position data.

Next, in a second calibration computation step, the marks in FIG. 26 are used to measure the calibration data with higher precision. In this case, instead of the movement information of the eyeball, the gaze position data output based on the calibration data determined in the first calibration computation step is used to convert the coordinates of the gaze point and the coordinates of the transmission point with high precision according to formulas having many coefficients as the formulas [Math. 1] to [Math. 4].

The calibration divided into a plurality of steps is convenient since it allows use of the calibration function of the conventional line of sight detection device. The conventional device, which fails to cope with errors due to the refractive action at the lens of eyeglasses, fails to perform high precision calibration at the peripheral part of the field of view. However, the conventional device has a part of the function of the first calibration computation unit to acquire the movement information of the eyeball and acquire the gaze position data from the acquired movement information of the eyeball and for the errors other than that caused by the refractive action at the lens of eyeglasses, measures to cope with such is expected to be taken. The conventional device that outputs no such movement information of the eyeball can be utilized by performing the calibration in divided steps.

As explained above, this embodiment enables the movement information of the eyeball to be exactly calibrated over the whole field of view of the subject wearing the progressive power eyeglasses 116. This enables exact determination of the point at which the line of sight passes through the lens of the progressive power eyeglasses 116 over the whole region of the field of view in case the line of sight detection device 110 is used.

The present invention is not limited to this embodiment and various modifications may be made as appropriate without departing the gist of the present invention. Although this embodiment is explained the calibration computation is achieved at the calibration computation device 119, for instance, it may be achieved by arithmetic processing at the control device CONT by using software. In particular, the calibration may be into a plurality of stages using the conventional device, with a preceding stage being carried out by processing with hardware and a subsequent stage being carried out by processing on the PC using software. This processing may be carried out real-time while the subject 3 gazes at a target object or may be subjected to post-processing using the stored image if the processing speed is limited.

For any spectacle lens that has a progressive power surface, which is its rear surface, the coordinates of the transmission point measured at the front surface can be approximately converted into the coordinates of the transmission point at the rear surface reflecting the angle of line of sight and the refractive mark of the lens of the spectacle lens.

The marks for calibration is not limited to those shown in FIG. 26. For instance, similarly to the second embodiment, the marks shown in FIG. 23A to FIG. 23 D may be used.

Figure 32:
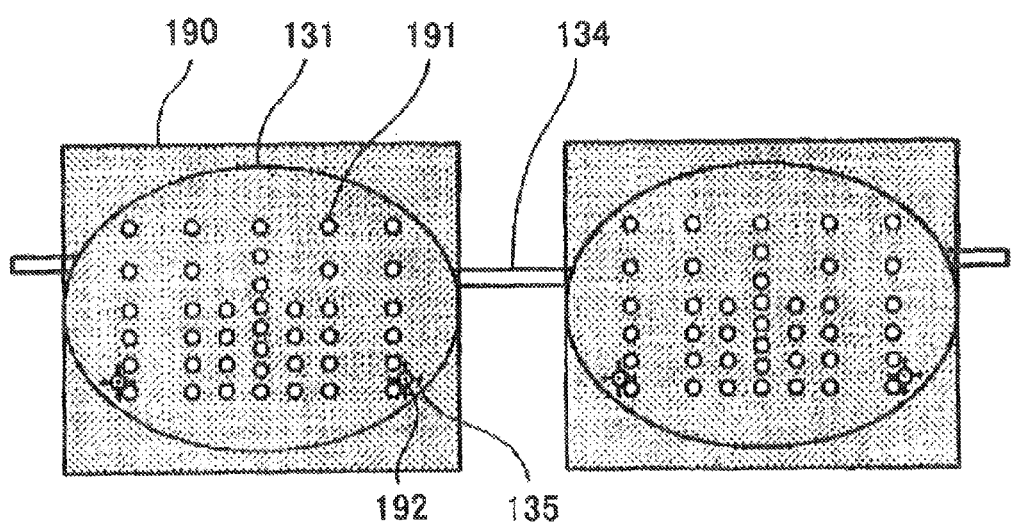
FIG. 32 is a diagram showing another constriction of the line of sight detection device according to the fourth embodiment of the present invention.

The method of measuring the calibration data for actual transmission position at the lens of the progressive power eyeglasses is not limited to the above-mentioned method. For example, a spectacle lens 131 having a film 190 in which a pinhole 191 is arranged as shown in FIG. 32 may be used upon measurement of the calibration data. However, the pinholes 191 need be arranged in the range and at the density the same as those in the case of the marks 121 for calibration. This enables high precision calibration of transmission position data all over the field of view including the peripheral part of the field of view or the progressive power part of the progressive power lens.

The film is provided with a pinhole 192 for positioning. Superimposing the pinhole on the mark 135 on the spectacle lens provides the position of each pinhole relative to the spectacle lens.

This film may be a filter that transmits infrared light but shields visible light, for instance, KODAK Wratten 2 filter for infrared photography. In this case, the movement information of the eyeball and the position of each pinhole on the spectacle lens can be measured while the subject gazes at a distance target through each pinhole of the film attached to the spectacle lens. The calibration data for the gaze position data in this method is separately measured by the above-described method.

The line of sight detection device may be attached to the head of the subject by a method other than the method illustrated in FIG. 25. Any type of device may be used that measures the movement of the eyeball of the subject. For instance, the present invention may be adopted in any device of the stationary type that has a function of detecting the direction of the eyeball relative to the head of the subject. Also, the present invention may be adopted in a device of the stationary type that lacks such a function in combination of a separate device that is capable of detecting the movement of the head of the subject.

The above described embodiments are exemplary and various modifications can be made without departing from the scope of the invention.

What is claimed is:

1. A line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, the method comprising:
   a measurement step of measuring the movement of the eyeball of the subject in a condition in which a first baseline is arranged at an outer peripheral part of the lens of the eyeglasses and a corner cube at which the subject gazes is adjusted such that the first baseline reflected in the corner cube substantially corresponds to a second baseline of the corner cube; and
   a calibration step of calibrating the line of sight detection device based on a result of measurement by the measurement step, wherein
   the second baseline is at least one of a ridgeline of the corner cube and a reflected image of the ridgeline.

2. The line of sight detection device calibration method according to claim 1, wherein the first and the second baselines are baselines in at least two different directions, respectively.

3. The line of sight detection device calibration method according to claim 1, wherein
in the measurement step, the movement of the eyeball of the subject is measured in the condition in which the subject holds the corner cube in the subject's hand.

4. The line of sight detection device calibration method according to claim 1, wherein
the first baseline is depicted on a reference member attached to the outer peripheral part of the lens of the eyeglasses.

5. The line of sight detection device calibration method according to claim 1, wherein
the eyeglasses are a frame for ocular examination and
the first baseline is depicted on the frame for ocular examination.

6. A line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, the method comprising:
a detection step of detecting a position of a corner cube in a condition in which a first baseline is arranged at an outer peripheral part of the lens of the eyeglasses and the corner cube at which the subject gazes is adjusted such that the first baseline reflected in the corner cube substantially corresponds to a second baseline of the corner cube; and
a calibration step of calibrating the line of sight detection device with respect to the transmission point based on a result of detection by the detection step, wherein
the second baseline is at least one of a ridgeline of the corner cube or a reflected image of the ridgeline.

7. A line of sight detection device calibration method, which calibrates a line of sight detection device that measures movement of an eyeball of a subject wearing eyeglasses and detects a transmission point at which a line of sight of the subject passes through a lens of the eyeglasses based on a result of measurement, the method comprising:
a detection step of detecting a gaze point of the subject in a condition in which a first baseline is arranged at an outer peripheral part of the lens of the eyeglasses and a corner cube at which the subject gazes is adjusted such that the first baseline reflected in the corner cube substantially corresponds to a second baseline of the corner cube; and
a calibration step of calibrating the line of sight detection device with respect to the transmission point based on the result of the detection by the detection step, wherein
the second baseline is at least one of a ridgeline of the corner cube and a reflected image of the ridgeline.

8. A line of sight detection device which measures movement of an eyeball of a subject wearing eyeglasses and detects a transmission point at which a line of sight of the subject passes through a lens of the eyeglasses based on a result of measurement, wherein
the device is calibrated by the line of sight detection method according to claim 1.

9. A spectacle lens design method comprising:
analyzing data of the transmission point obtained by the line of sight detection device according to claim 8; and
designing a lens of eyeglasses based on a result of the analyzing.

10. A spectacle lens selection method comprising:
analyzing data of the transmission point obtained by the line of sight detection device according to claim 8; and
selecting at least one lens of eyeglasses among a plurality of lenses of eyeglasses based on a result of the analyzing.

11. A spectacle lens manufacturing method comprising:
analyzing data of the transmission point obtained by the line of sight detection device according to claim 8; and
manufacturing a lens of eyeglasses based on a result of the analyzing.

12. The line of sight detection device calibration method according to claim 6, wherein
in the measurement step, the movement of the eyeball of the subject is measured in the condition in which the subject holds the corner cube in the subject's hand.

13. The line of sight detection device calibration method according to claim 7, wherein
in the measurement step, the movement of the eyeball of the subject is measured in the condition in which the subject holds the corner cube in the subject's hand.

14. A line of sight information detection method, comprising:
calibrating a line of sight detection device by the line of sight detection device calibration method according to claim 1; and
detecting a transmission point by the line of sight detection device.

15. A spectacle lens design method comprising:
analyzing data of the transmission point obtained by the line of sight information detection method according to claim 14; and
designing a lens of eyeglasses based on a result of the analyzing.

16. A spectacle lens selection method comprising:
analyzing data of the transmission point obtained by the line of sight information detection method according to claim 14; and
selecting at least one lens of eyeglasses among a plurality of lenses of eyeglasses based on a result of the analyzing.

17. A spectacle lens manufacturing method comprising:
analyzing data of the transmission point obtained by the line of sight information detection method according to claim 14; and
manufacturing a lens of eyeglasses based on a result of the analyzing.

* * * * *